United States Patent
Clare

(10) Patent No.: US 8,517,912 B2
(45) Date of Patent: Aug. 27, 2013

(54) MEDICAL HYPNOSIS DEVICE FOR CONTROLLING THE ADMINISTRATION OF A HYPNOSIS EXPERIENCE

(75) Inventor: Jon Clare, Kent (GB)

(73) Assignee: Neurocoach Limited, Petts Wood (GB)

( * ) Notice: Subject to any disclaimer, the term of this patent is extended or adjusted under 35 U.S.C. 154(b) by 1194 days.

(21) Appl. No.: 12/373,809

(22) PCT Filed: Jul. 20, 2007

(86) PCT No.: PCT/GB2007/002800
§ 371 (c)(1),
(2), (4) Date: Feb. 24, 2009

(87) PCT Pub. No.: WO2008/009978
PCT Pub. Date: Jan. 24, 2008

(65) Prior Publication Data
US 2010/0010289 A1  Jan. 14, 2010

(30) Foreign Application Priority Data

Jul. 20, 2006 (GB) .................................. 0614458.8
Mar. 1, 2007 (GB) .................................. 0704021.5

(51) Int. Cl.
*A61M 21/00* (2006.01)
(52) U.S. Cl.
USPC ............................................ 600/27; 600/545
(58) Field of Classification Search
USPC .................. 600/26–28, 300; 128/897–898
See application file for complete search history.

(56) References Cited

U.S. PATENT DOCUMENTS

| 4,883,067 | A | | 11/1989 | Knispel et al. | |
| 5,036,858 | A | * | 8/1991 | Carter et al. | 600/545 |
| 5,135,468 | A | * | 8/1992 | Meissner | 600/28 |
| 5,667,470 | A | | 9/1997 | Janata | |
| 5,725,472 | A | * | 3/1998 | Weathers | 600/21 |
| 5,899,867 | A | * | 5/1999 | Collura | 600/545 |
| 6,896,655 | B2 | * | 5/2005 | Patton et al. | 600/300 |

(Continued)

FOREIGN PATENT DOCUMENTS

DE 4344987 A1 7/1995
DE 100 28 787 A1 1/2001

(Continued)

OTHER PUBLICATIONS

International Search Report, Application No. PCT/GB2007/002800, 3 pages, Oct. 25, 2007.

*Primary Examiner* — Charles A Marmor II
*Assistant Examiner* — Carrie R Dorna
(74) *Attorney, Agent, or Firm* — Knobbe, Martens, Olson & Bear, LLP

(57) ABSTRACT

A medical hypnosis device (20) for controlling the administration of a hypnosis experience to a user is described. The device comprises a stimulus output module (24) for outputting a first type of content via one or more media channels to a sensory output device (28a, 28b) for presentation to the user and a sensor data receiver (26) for receiving physiological feedback data from a sensor (32a, 32b, 32c) sensing a physiological parameter of the user. The device also comprises a processor (22) for comparing the received physiological feedback data with predetermined physiological data to detect a change in a neurological state of the user. The processor is arranged, on detection of such a change, to trigger the provision of a second type of content to the user via the stimulus output module.

48 Claims, 12 Drawing Sheets

(56) References Cited

U.S. PATENT DOCUMENTS

| | | | |
|---|---|---|---|
| 2001/0005770 A1* | 6/2001 | Blumenthal | 600/27 |
| 2002/0045960 A1* | 4/2002 | Phillips et al. | 700/94 |
| 2004/0230252 A1 | 11/2004 | Kullock et al. | |
| 2007/0049805 A1* | 3/2007 | Schillizzi et al. | 600/300 |

FOREIGN PATENT DOCUMENTS

| | | |
|---|---|---|
| EP | 0 422 253 A1 | 10/1989 |
| WO | 99/49822 | 10/1999 |
| WO | 2007/094427 A1 | 8/2007 |

* cited by examiner

Figure 11: Brain's responses (event-related potentials) to standard and deviant sounds

MEDICAL HYPNOSIS DEVICE FOR CONTROLLING THE ADMINISTRATION OF A HYPNOSIS EXPERIENCE

FIELD OF INVENTION

This invention relates to a medical hypnosis device for controlling the administration of a hypnosis experience. In particular, the invention relates to a hypnosis therapy related techniques as part of an integrated psychological therapy package, and more specifically to a hypnosis device and method, which automates the practice of hypnosis or autosuggestion therapy, and which improves control of administering hypnotic induction processes to a user.

BACKGROUND TO THE INVENTION

Personal health, development and performance are increasingly important concerns within our society. Over hundreds of years, hypnosis has continued to produce positive results in a very wide variety of subjects including health (mental and physical), performance enhancement, learning and personal issues/development.

Areas where results relating to hypnosis have been successfully proven include: Improved cancer survival rates, Cancer pain reduction, Severe pain control, Healing bones quicker, and Immune system strengthening.

Additionally, hypnosis is currently used extensively in many therapeutic realms including the treatment of anxiety, phobias, obesity, behavioral medicine and smoking cessation, as well as with more severe psychopathology and post-traumatic conditions.

The term 'hypnosis' typically denotes an interaction between one person, the 'hypnotist' or 'hypnotherapist', and another person or people, the 'subject' or 'subjects'. In this interaction the hypnotist attempts to influence the subjects' perceptions, feelings, thinking and behaviour by asking them to concentrate on ideas and images that may evoke the intended effects. Hypnosis and hypnotic procedures have two basic elements, trance and suggestion.

The term 'trance' relates to the user being in a sufficiently relaxed state such that they are susceptible to suggestions which are aimed directly at the user's subconscious mind. Although science has not clearly identified a unique and tangible 'hypnotic signature', namely a machine-detectable unique brainwave activity pattern which confirms that the subject has reached the desired hypnotic state, hypnosis therapy is still recognised through both research and practice to be a highly effective, wide-ranging and safe mental phenomena.

However, there are many negative connotations and pre/misconceptions that are connected to hypnosis in general. These factors have unfortunately limited the acceptance and usage across a wider population.

Some people believe that they will loose control of themselves and be open to unwanted suggestions not previously approved.

Over many years the media has frequently portrayed hypnosis inaccurately or sensationally, which has created numerous misunderstandings, misperceptions and clichés. Despite hypnosis simply being a state of sleep, people are still nervous that this hypnotic state will remain with them forever and prevent them from awaking.

Further problems associated with hypnosis therapy include an inherent inability to know when to deliver the key subject message (i.e. suggestions or instructions) for maximum effectiveness. This is because without an understanding of when the conscious mind has relaxed, the therapist has to estimate what they consider to be the most suitable time to deliver the instructional command about the hypnotic session subject matter. Currently science has no way of defining exactly when an individual is in hypnosis.

Traditionally, hypnotherapists use only external physical parameters to gauge the depth of hypnotic trance, including pace of breathing, flushing of checks, slumping of shoulders. The therapist may find defining the level of relaxation very difficult to assess. Additionally, they will find it very hard to determine how 'unengaged' or relaxed the conscious mind is at any given moment. This could result in the therapist delivering the important instructional suggestions (around the desired subject matter) when it could be much less effective than at other times in the induction. This reduces the overall effectiveness of the therapy.

Frequently in traditional practice, patients become too relaxed and fall into normal sleep. This is not a preferred state of mind for hypnosis to produce results and has limited benefit to the client. Unfortunately, the hypnotherapist is often not aware that they are asleep as they have limited capability to gauge the level of relaxation.

In addition, hypnosis as it is currently administered is typically only successful for a small percentage of people/users (approx 2 out of every 10 people). This may be as a result of the above problems of not knowing when a subject is in a susceptible state.

Furthermore, hypnotherapists often use the same repeated script (or collection of hypnotic techniques) that they are familiar with, delivering this script with their own voice. Often there is a limited variety of techniques and familiarity of content is valued above actual effectiveness.

People are individual, and not all techniques work with everyone. With traditional delivery of hypnosis, it is impossible to determine the extent of individual success and personal appropriateness that a particular techniques may have.

Furthermore, no therapist can be an expert across every subject matter that they may be requested to use hypnosis to treat. Therefore, many therapists specialise only in a small number of subjects. This may mean that users find it difficult to find a specialist for their subject area. Some hypnotherapists may try and administer in subjects that they have limited experience or understanding of, using a simple generic hypnotic process. However, typically this method does not result in success.

Basic hypnosis may be delivered using multi-media delivery methods. This involves providing a standard hypnosis instruction continuously: the hypnotic instruction is not personalised or tailored in any way to the individual user and as there is no feedback, this delivery mechanism suffers from the same problems discussed above in that a user may not be in a susceptible state when the hypnosis instructions/suggestions are delivered.

Current methods of hypnosis delivery cannot administer personalised therapy to more than one patient at a time. This limits the number of patients any therapist can treat at any time to one. As hypnotherapists can only administer to one patient at a time, session costs are high as they are required to cover the therapists exclusive time with each patient There is very little understanding of the varied impact that different content may have on the success of an induction. For example some content may ask a user to start visualising before the user is in a state of mind that supports visualisation (or at least maximises the likelihood of being able to visualise). Other content may require a user to mentally (or consciously) engage in an exercise. However, the user may be very relaxed and this may disturb their depth of relaxation and therefore the success of the experience.

Increasing healthcare costs and an ever increasing desire to reach greater levels of performance means that there is a growing need for an alternative therapy that can bring quantifiable benefits in a very wide variety of subjects.

Hypnosis may be used to treat a wide variety of areas, including: pain control and relief, migraine and headache reduction, irritable bowel syndrome, immune system boosting, arthritic pain, sports performance, erectile dysfunction, treatment of warts, preparing for surgery, smoking cessation, weight loss, treatment of anxiety, obesity, hay fever, hypertension and stress, asthma, haemophilia, memory improvement, concentration level improvement, improved self discipline, post traumatic stress, dentistry, child birth, sexual performance, fears, phobias, self perception, speed reading, sales skills, presentation skills, improved relationships, attention deficit disorders, and learning disabilities. It is to be appreciated that this list is not exhaustive.

In addition, it is desirable that this therapy be available at an affordable price without any side effects.

STATEMENTS OF INVENTION

According to one aspect of the present invention there is provided a medical hypnosis device for controlling the administration of a hypnosis experience to a user, the device comprising: outputting means for outputting a first type of content via one or more media channels to a sensory output device for presentation to the user; receiving means for receiving physiological feedback data from a sensor sensing a physiological parameter of the user; and processing means for comparing the received physiological feedback data with predetermined physiological data to detect a change in a neurological state of the user, the processing means being arranged, on detection of such a change, to trigger the provision of a second type of content to the user via the outputting means.

This medical hypnosis device offers the advantage that it is possible to determine when a user is in a 'susceptible' deeply relaxed state such that instructions and suggestions can be directed at the user's subconscious mind at an appropriate time, and as a result the hypnosis experience is successful.

The term user relates to a person who is the subject of the hypnosis session.

Conveniently, the medical hypnosis device may further comprise a sensor, the sensor being arranged to measure the physiological parameter.

Typically, the sensor may be arranged to measure a physiological parameter which is one of a group comprising brainwave activity, galvanic skin response, heart rate variability, and rate of breathing.

Suitably, the device may comprise a plurality of different sensors measuring a plurality of different physiological parameters simultaneously.

Conveniently, the processing means may comprise state determining means for determining the current neurological state of the user using the received physiological feedback data.

Advantageously, the state determining means typically may be configured to determine the neurological state of the user by corroborating the received physiological feedback data from one of the plurality of sensors with the received physiological feedback data from another one of the plurality of different sensors.

The received physiological feedback data typically may comprise a complex multiple frequency signal, and the processing means suitably may be arranged to determine a predominant frequency signal from the complex multiple frequency signal.

Suitably, the brainwave activity may be measured using a technique which comprises electroencephalography (EEG) or functional magnetic resonance imaging.

Typically, the predominant frequency may be within one of a plurality of frequency bands (e.g. alpha, beta, theta, gamma, and delta) and wherein the processing means may be arranged to detect the change in the neurological state of the user at a point in time when the predominant frequency changes from being in one frequency band to being in another frequency band.

Typically, the content may be an output signal comprising an audio signal or a display signal.

The content typically may be a display signal for driving a visual display device to generate a virtual reality representation of the user achieving a particular goal.

The content optionally may be an output signal for driving a device which stimulates the user's smell, taste or touch senses.

Conveniently, the outputting means may be arranged to output a stereo audio signal, comprising a first audio signal for presentation to a first ear of the user and a second audio signal for presentation to a second ear of the user, the first audio signal comprising a first frequency signal and the second audio signal comprising a second frequency signal, wherein the first and second frequency signals are selected for the provision of a binaural beat audio signal.

Suitably, the outputting means may be arranged to output a stereo audio signal, comprising a first audio signal for presentation to a first ear of the user and a second audio signal for presentation to a second ear of the user, wherein the second audio signal may be a delayed version of the first audio signal.

Optionally, the second audio signal may have a greater amplitude than the first audio signal.

Conveniently, the medical hypnosis device may further comprise selecting means for selecting the content to be output by the outputting means from a plurality of stored content data segments.

Suitably, the content selecting means may arranged to execute a content selection rule to determine whether a selected segment can be output sequentially before or after another segment.

The content selecting means optionally may be arranged to prevent the selected segment from being output if the content selection rule determines that the selected segment should not be output.

Conveniently, each segment may comprise at least one metadata tag describing attributes of the content segment and the content selecting means is arranged to select content segments using the metadata tag.

The at least one metadata tag typically may be arranged to specify one or more of the following content description items: content segment number, content narrator, content type, and content sub type.

Advantageously, the selecting means may further comprise a text-to-speech engine arranged to select text content from a plurality of stored text content data segments and convert it into an audio speech signal to be output by the outputting means.

Suitably, the device may be arranged to control a hypnosis session comprised of a plurality of sequential experience stages, the session including an introductory stage, a relaxation stage, an induction/suggestion/instruction stage, and an awakening stage, each stage relating to a current neurological state of the user as the session progresses.

Conveniently, the selecting means may be arranged to select a most appropriate data segment to be outputted by the outputting means on the basis of the sensed neurological state of the user, the current stage of the session, and a desired subsequent stage of the session.

The selecting means suitably may be arranged to determine the next segment to be selected for output on the basis of one or more of the following criteria: the content type, content attributes, a session history of which segments have previously been output.

Conveniently, the medical hypnosis device may further comprise time management means arranged to determine from a desired length of time of the session and an expired time, a length of time remaining for the session, wherein the selecting means may be arranged to select the most appropriate data segments in accordance with the length of time remaining for the session.

Typically, the selecting means may be arranged to enable an administrator to select data segments.

Advantageously, the device may be arranged to receive user-specified preferences regarding data selection and the selecting means may be arranged to select the data segments in accordance with the user-specified preferences.

The medical hypnosis device may further comprise learning means arranged to learn using the feedback data which data segments, after they have been outputted to the user, are the most effective data segments for encouraging the user to progress through the current stage of the session; and storing means for storing the most effective data segments in a database record associated with the user.

Advantageously, the medical hypnosis device can learn what content is successful with a user and what content is not, meaning that each time a user uses the medical hypnosis device to deliver a hypnosis experience, the medical hypnosis device is able to deliver better tailored content and increasingly successful hypnosis experiences.

Conveniently, the medical hypnosis device may further comprise profiling means arranged to administer a profiling test to the user prior to the hypnosis experience; and result determining means arranged to determine the results from the profiling test; wherein the selecting means may be arranged to select the most effective data segments for encouraging the user to progress through the different stages of the session.

Suitably, the medical hypnosis device may further comprise profile result storing means for storing the profile test results, and the most effective data segments in a database record associated with the user.

Typically, the medical hypnosis device may further comprise means for determining baseline readings for user, the baseline readings being representative of the physiological readings obtained by the device when the user is in an alert neurological state without being provided with a stimulus, and for using stored baseline readings for comparison during the hypnosis session.

The medical hypnosis device typically may further comprise recording means arranged to record all activity within a session to provide a full audit trail of every session.

Advantageously, results of each session may be analysed such that the medical hypnosis device may be able to further tailor the provision of content for particular users in subsequent hypnosis sessions.

Conveniently, the medical hypnosis device may further comprise real-time monitoring means arranged to monitor progression of the user through the hypnosis experience in real-time.

The real-time monitoring means may advantageously include a feedback channel including a microphone arranged to enable an administrator to output content to the user verbally during a hypnosis session.

This is advantageous as it enables an administrator to add highly individual and tailored content to a user, to improve the hypnosis experience.

The real-time monitoring means may typically comprise display means for displaying a graphical representation of the content output to the sensory output device.

Suitably, the medical hypnosis device may further comprise means for downloading content or an application for configuring the device from a remote source via the internet.

In one embodiment, the outputting means may be arranged to output movement instructions to the user and the sensor may comprise a motion sensor.

According to one aspect of the invention there is provided a games console configured to operate as the medical hypnosis device described herein.

According to another aspect of the invention there is provided a combination of the medical hypnosis device described herein, and a sensory output device for presenting content to a user.

BRIEF DESCRIPTION OF DRAWINGS

FIG. 7a is a three-dimensional schematic diagram of frequency components similar to FIG. 6a highlighting a section of time during which 'alpha-theta crossover' occurs;

FIG. 7b is an example graph of voltage versus time for the section of time highlighted in FIG. 7a;

DETAILED DESCRIPTION

A system comprising a hypnosis device that outputs stimulus to a user and receives physiological information feedback from the brain and/or body of the user is described which embodies the present invention. The system uses the received physiological information feedback to control a user's hypnosis experience assisting a user achieving their goals more effectively.

The system incorporates machine generated learning and intelligence to automatically drive pre-recorded induction sensory related 'clips' in a wide range of users (health, performance enhancement, learning, personal development/issue etc), delivering each stage of the induction at the time of derived optimal effectiveness. The delivery and selection of sensory content, such as audio/visual content, is controlled using feedback data relating to a condition of the current state of the users' consciousness and the level of relaxation and makes for a far better and more accurate system of delivering hypnosis therapy.

A hypnosis session includes relaxation, message delivery and wake-up or rousing.

To be effective, message delivery must occur at a time when the user is suitably relaxed, inattentive, absorbed in the experience and in a trance-like state but not too relaxed, i.e. in an unconscious state. The term 'relaxed', in relation to a user, is taken to mean that the user is relaxed and inattentive and that the user is absorbed in the hypnosis experience. A corresponding meaning applies to the terms 'relaxing' and 'relaxation' used throughout the description.

Figure 1:
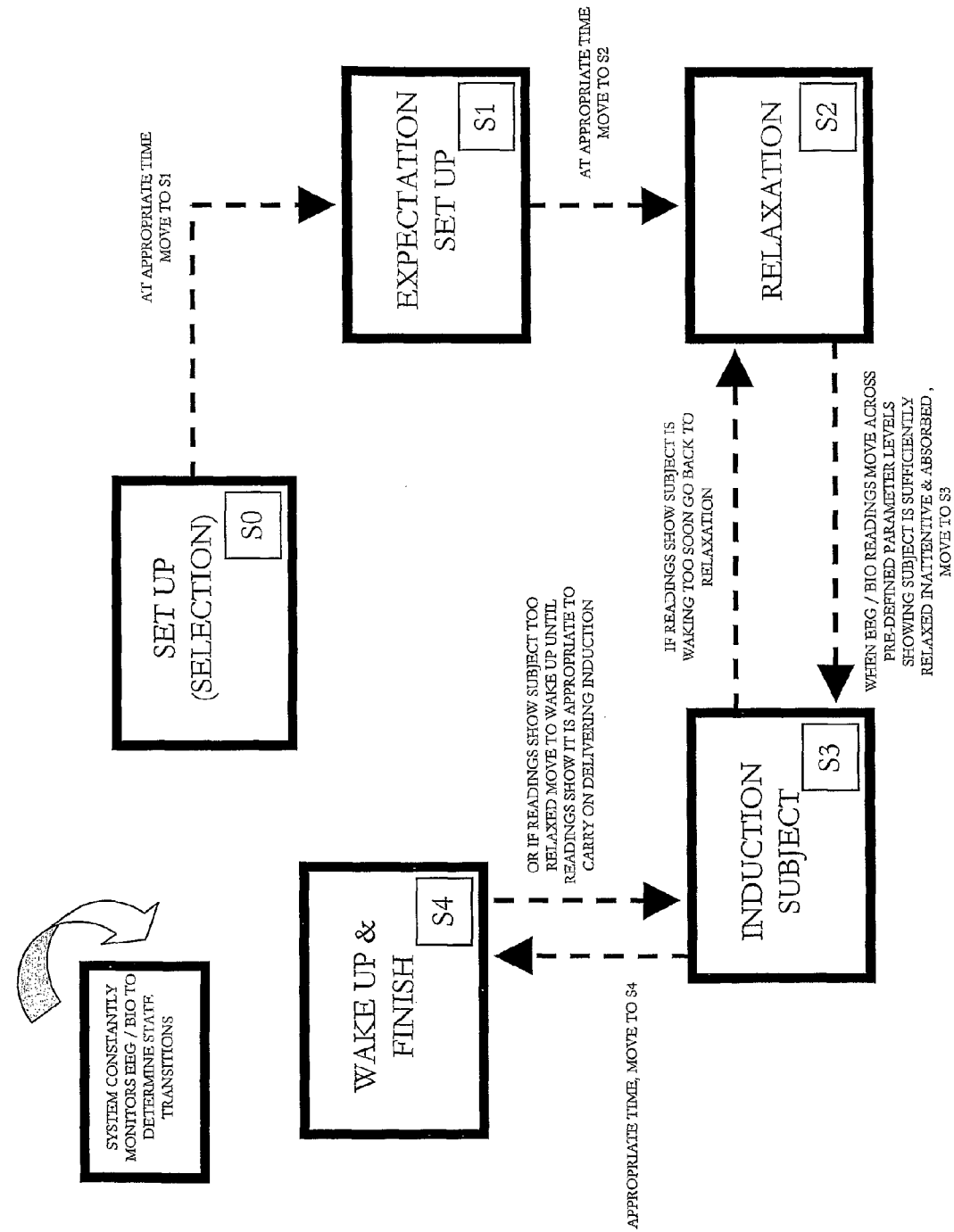
FIG. 1 is a state diagram showing five different stages of a hypnosis experience.

An overview of a hypnosis experience/session, administered by the system is described in relation to a state/stage diagram shown in FIG. 1.

The user experiences, at stage S0, a set-up phase of the hypnosis session. The set-up phase includes a selection phase, which permits the user to configure session requirements of the hypnosis session, i.e. what result does the user want to achieve from the hypnosis session, for example, an improvement in a particular sport or cessation of smoking etc.

These session requirements may be gathered by an administrator during a profiling interview with the user. Alternatively, the user may enter suitable details themselves via a graphical user interface associated with the hypnosis device. Other session requirements include selection of a preferred narrator and language. In addition, preferred content may be selected.

Stage S0 also includes applying one or more sensors to the user's body. Measurements from the sensors are described in more detail later. However, typically the sensors include those suitable for obtaining electroencephalogram (EEG), electrocardiogram (ECG), galvanic skin response (GSR), and/or heart rate variability (HRV) readings.

During stage S0, while the user is alert, the sensors are tested to ensure good outputs are received. In addition, testing may include obtaining baseline readings for each of the different sensors, such that during the hypnosis session a deviation from the baseline reading may be calculated and used in determining subsequent actions to be taken by the hypnosis device.

The move to the next stage is triggered by the user or administrator indicating that both the system and the user are ready to proceed. This is typically achieved via a button, microphone or on-screen touch pad.

A continuous stream of content clips are played to the user throughout the hypnosis session. Content clips may include audio and/or visual clips. Audio may be played via six different channels, i.e. three channels being speech, background music, and sound effects, for each of the two ears. Visual clips may be played via a display device of the system.

The system may play individual speech content clips in stereo. Alternatively, the system has the capability to take advantage of overlaid sounds. This allows the system to utilise complicated aural techniques such as binaural beats or double induction, as well as various speech and background music combining techniques.

Content may also be derived using text-to-speech drivers. As a result, the content may be highly variable and may be tailored for a user, regarding a particular suggestion or message without the requirement of having a narrator record a plurality of clips. Sophisticated text-to-speech drivers can make a speech audio stream sound natural, such that a user will not be able to tell that the audio originates from a text-to-speech driver.

Text-to-speech conversion may be done on-the-fly from previously generated text or from text generated at the time of the hypnosis session, or shortly before. Storage of text, which may then be used for generating audio content for the hypnosis session, may reduce data storage overheads.

The text-to-speech driver punctuates the text to be converted in a particular (machine-readable) format such when converted into speech, the speech sounds natural. Reading software subsequently reads the punctuated language and converts it into speech to be played to the user at the required time.

Content is played at stage S1 which acts as an introduction for the user to the present hypnosis session, and is designed to set-up the expectations of the user for the upcoming session.

Stage S1 also provides important instructions for the user (including practical information e.g. "if the fire alarm goes off you will wake immediately" etc). This information may be delivered through both audio and visual means. Additionally, it may be designed to reduce the user's anxiety and provide information about what the user can expect to experience.

Transition from this period is not typically driven by neurological or physiological measurements or events, but is based on the amount of time that the session is due to last (i.e. stage S1 lasts for a set amount of time based on the chosen time length of the hypnosis experience). When the time allocated for stage S1 expires, the system will move to stage S2. Towards the end of this period (stage S1), the user is typically instructed to close their eyes.

Content designed to relax, distract and create an inattention (being an inattentive state of mind) within the conscious mind of the user is played at stage S2. This content is aimed at providing access directly to the subconscious mind of the user in the next stage. The content may involve relaxation exercises, calming music and sounds. In addition, the device is also monitoring, at stage S2, the user's state of relaxation. Based on the length of the total time the hypnosis event is due to last, there will be a minimum length of time that the relaxation content will be played. During this time the system will try to ensure that the user is fully relaxed. The system monitors neurological and/or physiological readings of the user to assess their state of relaxation. After a set time period (again governed by the total length of time of the induction) and providing the user is exhibiting a suitable degree of relaxation, the system moves to stage S3.

The conscious mind is now relaxed and/or distracted, and the objective of stage S3 is to play instructional content to the user via one or more output devices. The content is designed to be able to direct 'instructions' or 'suggestions' into the subconscious mind of the user. The instructions are specific to the subject (user) matter of the session, for example assistance with smoking cessation. The intention is to embed or amend thought processes that the subconscious mind will act upon.

If at any time during stage S3 the system detects that the user is no longer at a desirable level of relaxation (i.e. a deeply relaxed state), the system is configured to revert back to playing relaxation content to relax the user back to the desired level of relaxation or state. The system monitors any rise in consciousness/attention and determine if action (i.e. playing relaxation content) needs to be taken, based on how long or how swift the rise towards consciousness has been. Should the rise continue or persist after a certain time limit, the system may use other interventions (for example a binaural beat relaxation technique) to bring the user back towards the desired level of relaxation i.e. the deeply relaxed state. Once it is registered that the user is in the deeply relaxed state, the system continues to play suggestive or instructional content.

Conversely, sometimes a user may become too relaxed. Again the system, is able to detect such a change and the system reacts by playing 'wake-up' content specifically designed to try to wake the user to a more conscious level (i.e. "you are becoming too relaxed, please try and wake a little" etc). Once it is registered that the user is no longer 'over relaxed' the system will continue to play suggestive or instructional content.

Based on the total time that the hypnosis experience is scheduled to last, after a period of time the system will begin to wake the user. The content used at this point will be louder, more energetic and faster, encouraging the user to become more aware of themselves and their surroundings. During this period the content may embed post hypnotic commands and messages to strengthen any required behavioural or belief changes. Content at this point is also intended to boost the energy levels and positive feelings of the user once they finish the induction. Should the user fail to awaken from their relaxed state, an alarm sound (progressively increasing in volume) will be played until it is registered that the user has awoken.

Many different techniques may be used to assess a user's level of relaxation. Typically, such techniques measure neurological and physiological parameters, enabling the hypnosis device to determine, from the measurements, a neurological state of the user.

Measuring a neurological parameter includes measuring brainwave activity. One method of measuring brainwave activity is through the use of Electroencephalography (EEG). An electroencephalograph monitors the amount of brainwave activity emitted from the brain, measured through sensors which are placed on the scalp and connected to the hypnosis device.

EEG sensors are electrodes (of Silver/Silver Chloride construction) which pickup the electrical activity of the brain. Typically, a plurality of these electrodes are placed in contact with the scalp of the user: contact between the user's scalp and electrode being enhanced through the use conductive gel. The use of an appropriate electrode gel helps in converting the physiological (ionic) signals to electrical signals needed by the system, and will also help to reduce some 'noise'.

Each sensor is able to detect a complex multi-frequency signal, as different areas of a user's brain simultaneously emit signals of different amplitudes and frequencies. Relative amplitudes of different frequency components within complex multi-frequency signals can provide an indication relating to the level of relaxation of a user.

The complex multi-frequency signals are often referred to as brainwaves: the brainwaves relating to the electrical activity occurring at a particular area on a user's scalp where a sensor is attached. In an analogy, the sensors may be considered to be measuring the amplitude of peaks and troughs of ripples in a lake, the ripples being caused by a multitude of pebbles and rocks of different sizes being dropped at different areas in the lake. The sensors measure different amplitudes of waves, from different directions, at different times (i.e. frequency variations). The resultant signal being a complex multi-frequency signal of varying amplitude.

Brainwaves may be categorised into a plurality of different frequency bands as defined below. At any one time, the band that has the greatest strength/band-power is said to be the predominant band at that location and is an indication that a user is in an associated cognitive state relating to their level of relaxation.

The bands have associated upper and lower thresholds, and these may vary between different users. In one embodiment of the present invention, the system may monitor a user's brainwave patterns (and/or other physiological outputs) in order to determine the specific thresholds which are personalised for that user.

In one embodiment of the present invention, frequency elements of a user's brainwaves may be categorised into four different frequency bands, Beta, Alpha, Theta and Delta.

Beta is usually exhibited as the waking rhythm of the brain occurring when people are awake, focused and actively thinking. The electrical activity of this frequency is typically within the range of 14-26 times per second (or Hz).

The Alpha frequency indicates relaxed awareness and inattention. This begins to occur as an individual closes their eyes and starts to relax—reducing the level of information the brain is required to process from the senses. The electrical activity of this frequency is typically within the range of 8 and 13 Hz.

Theta occurs as an individual becomes deeply relaxed moving towards drowsiness. This state is linked to creativity, inspiration and deep meditation. The electrical activity of this frequency is typically within the range of 4 to 7 Hz.

Delta is associated with deep sleep, which borders on unconscious. The electrical activity of this frequency is typically within the range of ½ to 4 Hz.

Physiological parameters include heart rate, blood-oxygen levels, respiratory rate, body temperature, muscle activity (electromyogram), heart rate variability (HRV) and galvanic skin response (GSR). In addition, other physiological parameters may be measured or tested for example pressure sensors may be used to detect reductions in pressure being applied by the user, as they become more relaxed. Furthermore, motion sensors may be used to determine whether a user is reacting to instructions under hypnosis to move a particular part of their body, i.e. finger.

Heart rate may be measured using electrocardiography (ECG) or blood-volume pressure. The measured heart rate signals may be processed to extract inter-beat intervals and various heart rate variability (HRV) measurements. HRV is a measure of variations in a user's heart rate. It is usually calculated by analysing the time series of beat-to-beat intervals from the electrocardiogram, however, arterial pressure tracings may also be used.

An HRV measurement is taken over a period of time, for example five minutes, by placing a small infra-red sensor on the user's finger, or ear. During the measurement time, the heart rate is measured continuously in milliseconds. Measured this way, a healthy heart will show a wide variation of rate and the amount of this variation is measured. The greater the figure, the greater the variation.

HRV can be easily measured by means of a photoplethysmo sensor applied to a finger. The photoplethysmo sensor works through the emission and the reception of infrared light, which is absorbed from blood. The sensor finds the cyclical variations of the pressure tone in the capillaries of the fingers. These variations represent the cardiac beat faithfully. After the signal has been digitized, it is analyzed to calculate the exact distance between each successive heartbeat (this distance is expressed in milliseconds). In this way it is possible to create a diagram that expresses the distance between one heartbeat and another, in function of the number of heartbeats, known as a tachogram.

GSR is a method of measuring the electrical resistance of the skin. GSR is measured by attaching two electrodes to independent areas of the user's skin, for example a finger, while the electrical current that the skin is able to conduct is measured. A baseline reading is obtained while the user is alert and this baseline reading is compared with readings obtained during the hypnosis experience. Variations in GSR may be used as indicators of the level of relaxation of a user because GSR is highly sensitive to variations in a user's emotional state.

The above neurological and physiological parameters, along with other similar parameters, may be monitored in order to determine a neurological 'state' of a user such that selection of appropriate content may be made in order to further control the neurological state of the user.

Figure 2:
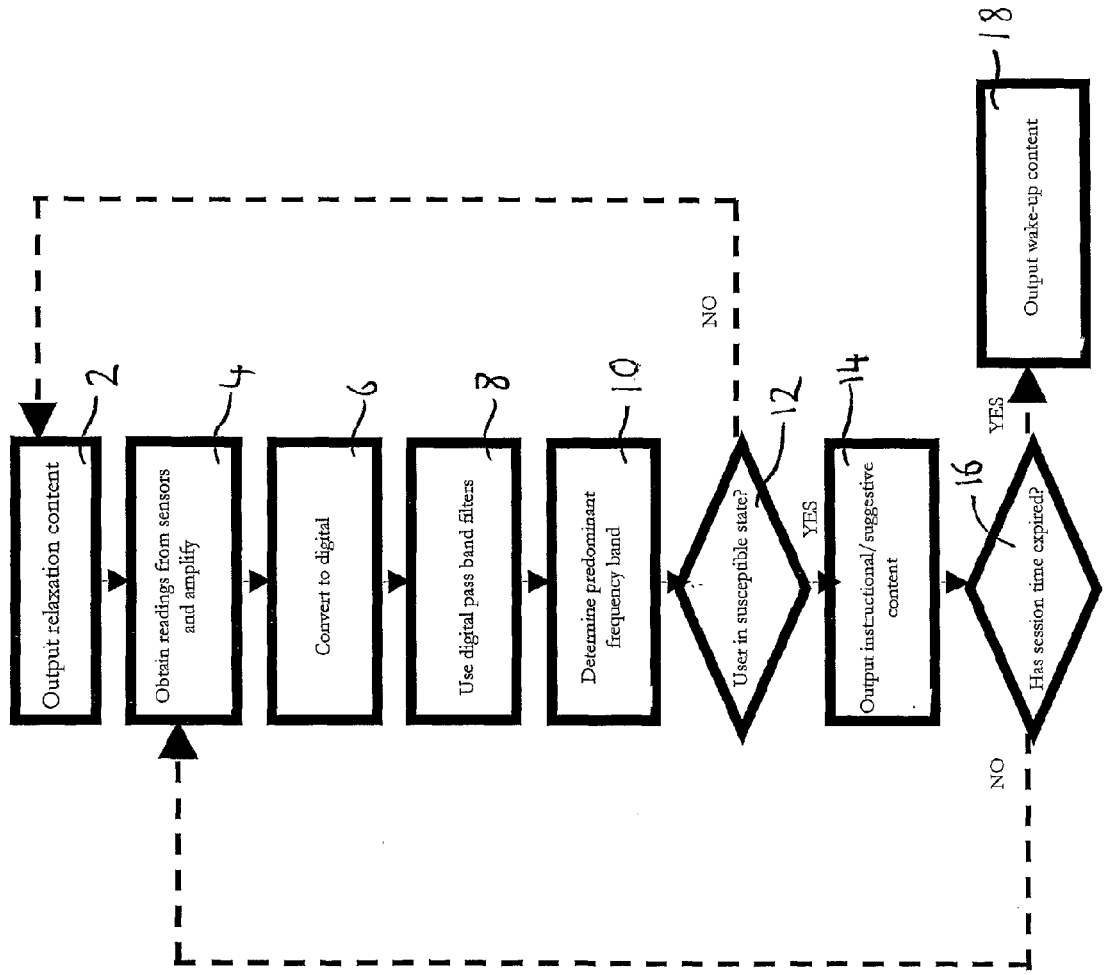
FIG. 2 is a flowchart of technical method steps of a medical hypnosis device in accordance with an embodiment of the present invention.

An overview of the technical method steps of operation of a medical hypnosis device is shown in FIG. 2. The overview of FIG. 2 relates to a medical hypnosis device which uses a technique referred to as 'alpha-theta crossover' to determine when the user is in a sufficiently relaxed or susceptible state such that provision of instructional content may begin. However, it is to be appreciated that this is not the only technique which may be used, as other indicators may be determined to enable the system to determine what state the user is in or whether a change of state has been registered. Other techniques are described in more detail below. Furthermore, it is to be appreciated that more than one technique may be used in combination to corroborate the state of the user.

As shown in FIG. 2, after the set-up and expectation stages, (S0 and S1 of FIG. 1), have been completed, a first type of content is played, at Step 2, to the user. The first type of content is relaxation content.

The output from each sensor is a multi-frequency analogue signal in the order of a few tens of micro-Volts (μV) is amplified and measured, at Step 4, and converted, at Step 6 into a digitised realisation of the analogue signal.

Typically, the signals from the EEG sensors contain noise which corrupts the useful data contained within the signal. Sophisticated signal processing techniques may be used to reduce this noise. For example, this may be achieved by correlating the signals from each sensor to identify elements of the measured signal which have been generated by the user's brain (as these signals should be identifiable in more than one signal) and background noise which may then be removed to improve the Signal-to-Noise Ratio.

In one embodiment, the signals from the sensors may be treated independently. However, in another embodiment, after the noise has been removed, the signals may be summed in order to provide an aggregate EEG reading: the aggregate reading being a multi-frequency complex signal.

Regardless of whether signals are summed or treated independently, the digital signal is passed, at Step 8, through a plurality of band-pass digital filters in order to separate frequency components of the signals into the a plurality of frequency bands. As described above, typically, four frequency bands may be of interest, beta, alpha, theta and delta.

Each frequency band has an associated band-power, i.e. the power or strength of the frequency components of the signal which fall within that particular band. Throughout a hypnosis session the frequency band which has the highest or predominant band-power is considered to be the predominant frequency band: the predominant frequency band providing an indication regarding the user's level of relaxation.

For example, if beta brainwaves are more predominant then the user may be considered as being awake and in an 'alert' neurological state. If alpha brainwaves are more predominant, the user may be considered as being in a 'relaxed awareness' neurological state. Whereas, if theta brainwaves are more predominant then the user may be considered as being in a 'deeply relaxed' neurological state. The deeply relaxed neurological state relates to a desired/target state which is suitable for delivering the hypnotic suggestions/instructions. A user is considered as being in a 'deep sleep' neurological state if delta brainwaves are more predominant.

As detailed above, approximate frequency bands for the four main bands are beta 14 Hz to 26 Hz, alpha 8 Hz to 13 Hz, theta 4 Hz to 7 Hz, and delta 0.5 Hz to 4 Hz. However, the hypnosis device provides for fine tuning these frequency bands as necessary by analysing session results, as described later.

Of particular interest during a hypnosis session is the crossover point between one band having a predominant band-power and another. In particular, the cross-over point between the alpha frequency band being predominant, and the theta frequency band being predominant, as this may be indicative that the user has passed between being in the relaxed awareness state to being in the deeply relaxed state. In one embodiment, this cross-over point may be used as a trigger to initiate (or continue) delivery of the hypnotic suggestions/instructions.

The system monitors, at Step 10 the band-powers of the alpha and theta frequency bands, and determines, at Step 12 whether there has been a cross-over between alpha and theta.

If there has been no change, the system continues to output, at Step 2, relaxation content. However, if there is a change, the system is arranged to output, at Step 14, a second type of content relating to the hypnotic suggestions/instructions.

The system also monitors the time throughout the hypnosis session and determines, at Step 16, whether the session time has expired. If the session time (less the amount of time required for the wake-up content) has not expired, the system continues measuring, at Step 4, the EEG signals. However, if the session time has expired, the system is arranged to output, at Step 18, the wake-up content to bring the user back to being awake and alert.

The device may be configured so as to prevent the user from rousing or from becoming too relaxed during the content delivery stage of the hypnosis session, by selecting appropriate corrective content should the system detect that the state of the user is no longer within the target state.

Figure 3:
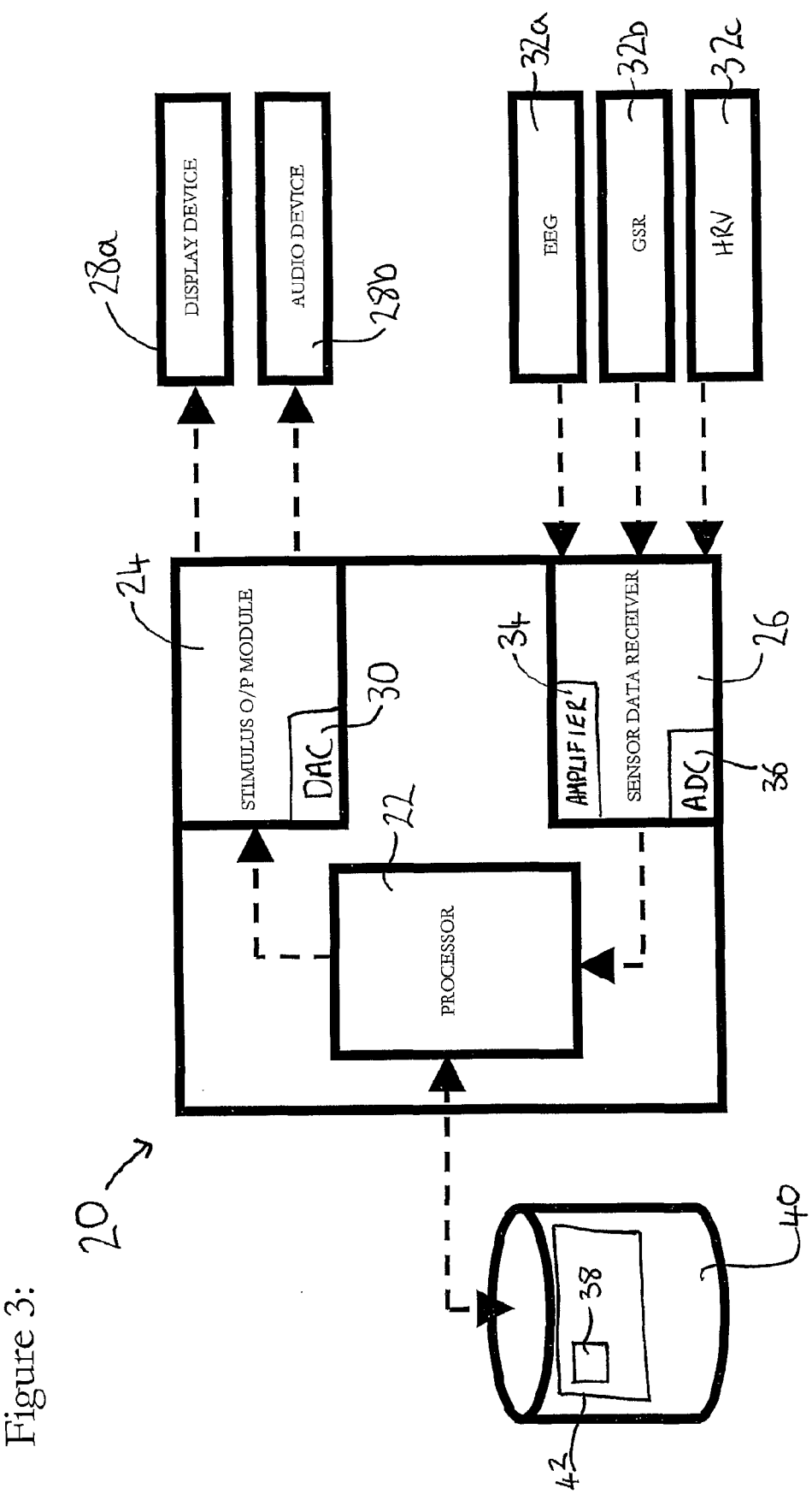
FIG. 3 is a schematic system diagram of an embodiment of the present invention comprising a processor, stimulus output module, sensor data receiver, database, output devices and sensors.

A block diagram of the system architecture is shown in FIG. 3. As shown, the medical hypnosis device 20 comprises a processor 22, stimulus output module 24, and a sensor data receiver 26.

The stimulus output module 22 is arranged to output stimulus content to output devices 28a, 28b, i.e. visual content to a display device 28a, and audio content to an audio device 28b. In one embodiment, the stimulus output module 24 is arranged to output different types of stimulus simultaneously. Stimulus is stored in a digital format and as such, the stimulus output module comprises a digital to analogue converter (DAC) 30 to convert the digital stimulus into analogue stimulus to be played to the user.

The sensor data receiver 26 is arranged to receive sensor data from one or more neurological or physiological sensors 32a, 32b, 32c. The sensor data receiver 26 may contain an amplifier 34 for amplifying the signals, and an analogue to digital converter (ADC) 36 for converting the analogue signals from the sensors 32a, 32b, 32c to a digital format, such that complex signal processing techniques may be carried out on the digital signals. It is to be appreciated that the amplification and conversion of the analogue signals may be carried out by the processor of the hypnosis device 20 or by an external device.

The rate at which the analogue signals are sampled by the ADC 36, in order to convert them into a digital format, is the sampling rate. The Nyquist sampling theorem stipulates that the minimum acceptable sampling rate is twice the highest frequency component in the signal being sampled. However, a higher sampling rate is desirable.

A typical sampling rate for sampling brainwaves using the present system is 240 Hz. This is adequate because brainwaves have frequency components which are typically in the region of 0.5 Hz to 60 Hz.

The processor 22 is arranged to determine from the sensor data an appropriate content clip 38 to next be output by the stimulus output module 24. The processor 22 has access to a database 40 which is arranged to store, in a content library 42, a plurality of clips of content which may be concatenated to create a continuous stream of content to be delivered to the user.

Figure 4:
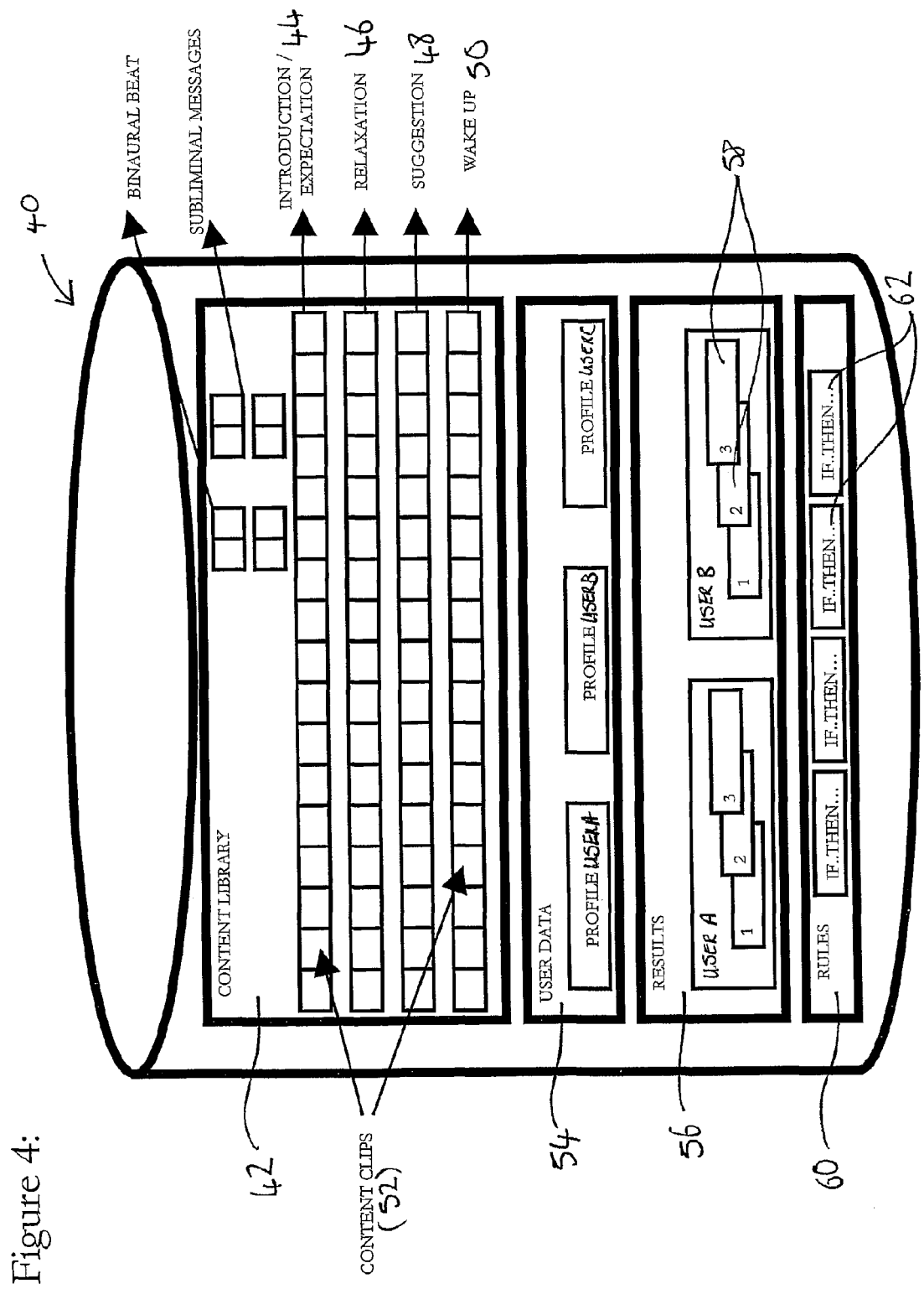
FIG. 4 is a schematic block diagram of the structure of a database of the system shown in FIG. 3.

As shown in FIG. 4, the content library 42 has sections for each of the different types of content, for example, introduction/expectation 44, relaxation 46, suggestions/instructions 48, and wake-up/alarm 50. Individual content clips 52 are stored in the content library 42, within each of the sections 44, 46, 48, 50. The content clips 42 are tagged with metadata to facilitate retrieval of the content at an appropriate time.

The database 40, shown in FIG. 4, also has: a user data section 54, for storing data relating to a plurality of users, including results of the profiling interview; a session results section 56, for storing the sessions and analysis results 58 from the hypnosis sessions of a plurality of users; and a rules section 60, for storing a plurality of rules 62 to be used by the system when determining the appropriate content clips 52 to be played.

Figure 5:
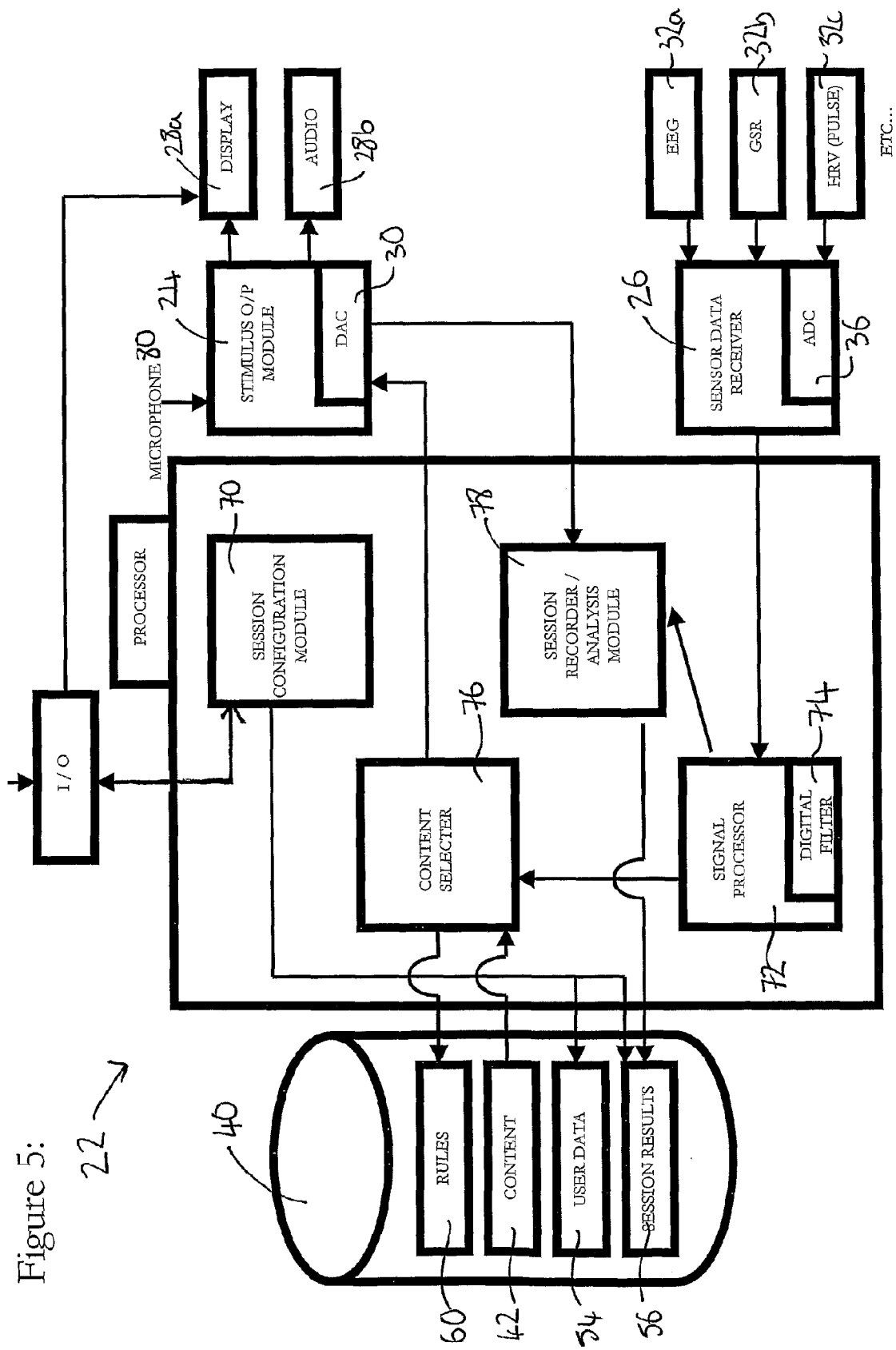
FIG. 5 is a schematic block diagram of the processor shown in FIG. 3 comprising a signal processor, content selector, session configuration module, and a session recorder/analysing module.

A functional block diagram of the processor 22 is shown in FIG. 5. As shown the processor 22 comprises: a session configuration module 70, for enabling user-configuration of a hypnosis experience; a signal processor 72 for performing signal processing on the received digitised data, including filtering by a digital filer 74; a content selector 76 for selecting appropriate content clips 52 based on the received digitised data and a target neurological state which is a function of the time remaining in the hypnosis session; and a session recorder/analysis module 78, for recording the content played to the user and the corresponding data received from the sensors 32a, 32b, 32c (via the signal processor 72).

As shown in FIG. 5, the stimulus output device 24 may be arranged to accept an input from a microphone 80 so that an administrator of the hypnosis session can provide additional aural content direct to the user. This is advantageous as it provides the functionality for an administrator to add very specific tailored instructions to the user. In one embodiment the hypnosis device may be used specifically to ensure that the user is in the deeply relaxed state so that they are susceptible to highly individual instructions which may be delivered, via the microphone 80, from the administrator.

The session configuration module 70 enables a user (subject) or an administrator to configure a plurality of session parameters for the hypnosis experience. The session parameters include a desired length of the session, a desired hypnotic suggestion/message, i.e. cessation of smoking; voice of recordings, music. In addition, the user/administrator is able to select preferences regarding content clips which should and should not be played. The session parameters are stored in the user data section of the database.

The signal processor 72 manipulates the digitised data in order for the data to be displayed as one or more waveforms on a display screen, or for recording by the session recorder for subsequent analysis. The signal processor 72 is also arranged to process the digital sensor data in order to provide suitable data to the content selector 76, such that appropriate content can be selected and played to the user.

The processing performed by the signal processor 72 depends on the type of analysis being performed in order to determine the user's neurological state. As described above, one method of assessing the user's neurological state involves monitoring which band of brainwave frequencies is more predominant. Other types of analysis which may be performed in order to determine the user's neurological state are described below.

Figure 6:
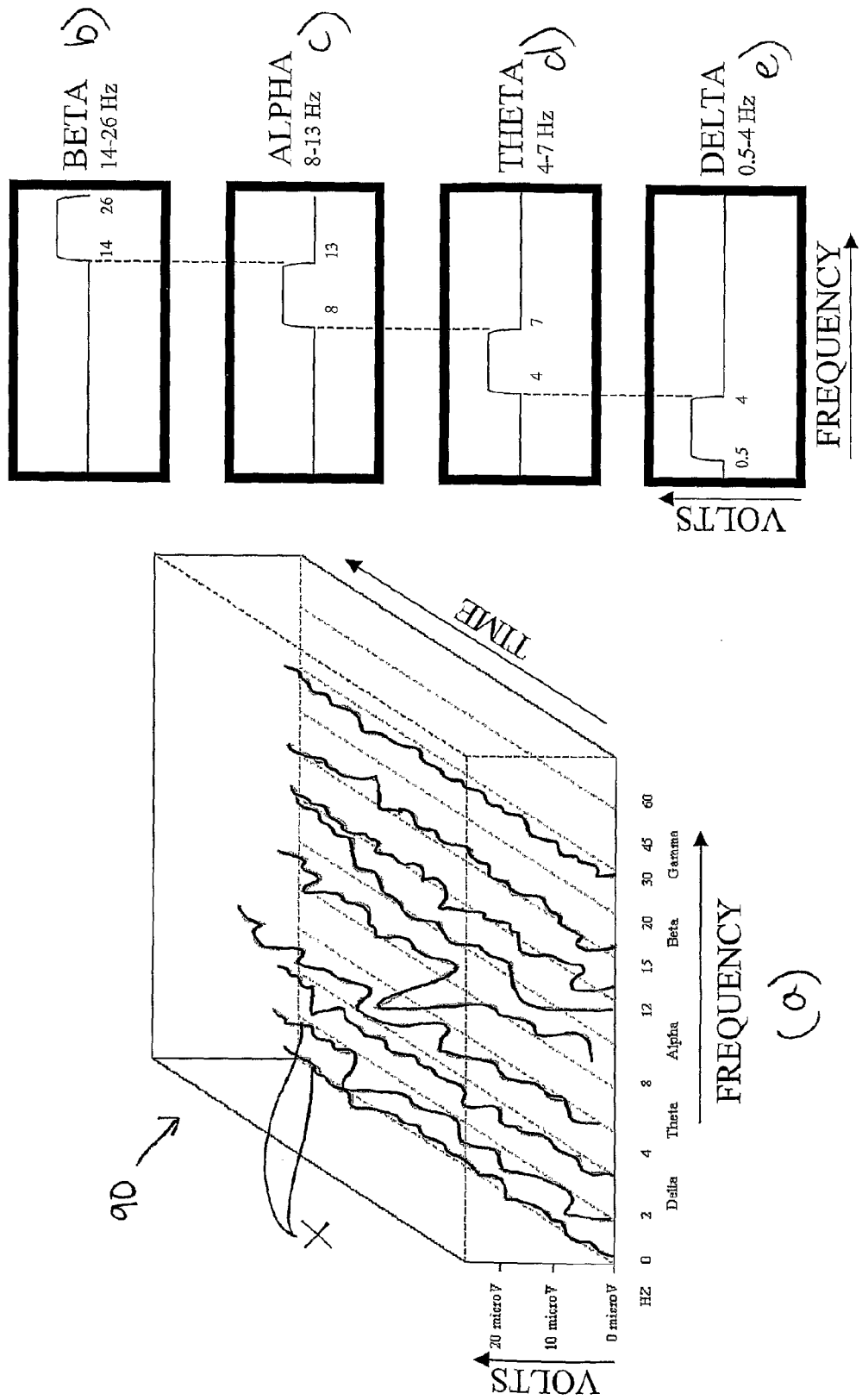
FIG. 6a is a three-dimensional schematic diagram of frequency components of a complex multi-frequency signal which is representative of a user's brainwaves.
FIGS. 6b to 6e are schematic diagrams of ideal frequency responses of four digital band-pass filters.

FIG. 6a shows a simplified three-dimensional representation 90 of complex multi-frequency brainwave signals. The X-axis represents frequency, the Y-axis represents voltage levels, and the Z-axis represents time.

A complex multi-frequency brainwave signal may contain a plurality of different frequency components and approximations of these have been shown in a plurality of individual waveforms X.

In order to extract the frequency components of a particular frequency band, the complex multi-frequency brainwave signal is passed through four digital band-pass filters, beta, alpha, theta and delta, shown in FIGS. 6b to 6e. For example, a frequency component of 20 Hz will pass through the beta digital band-pass filter, but will be attenuated by each of the alpha, theta and delta filters.

The signal processor 22 is arranged to determine which band is the most predominant band by calculating which frequency band has the highest band-power.

Figure 7:
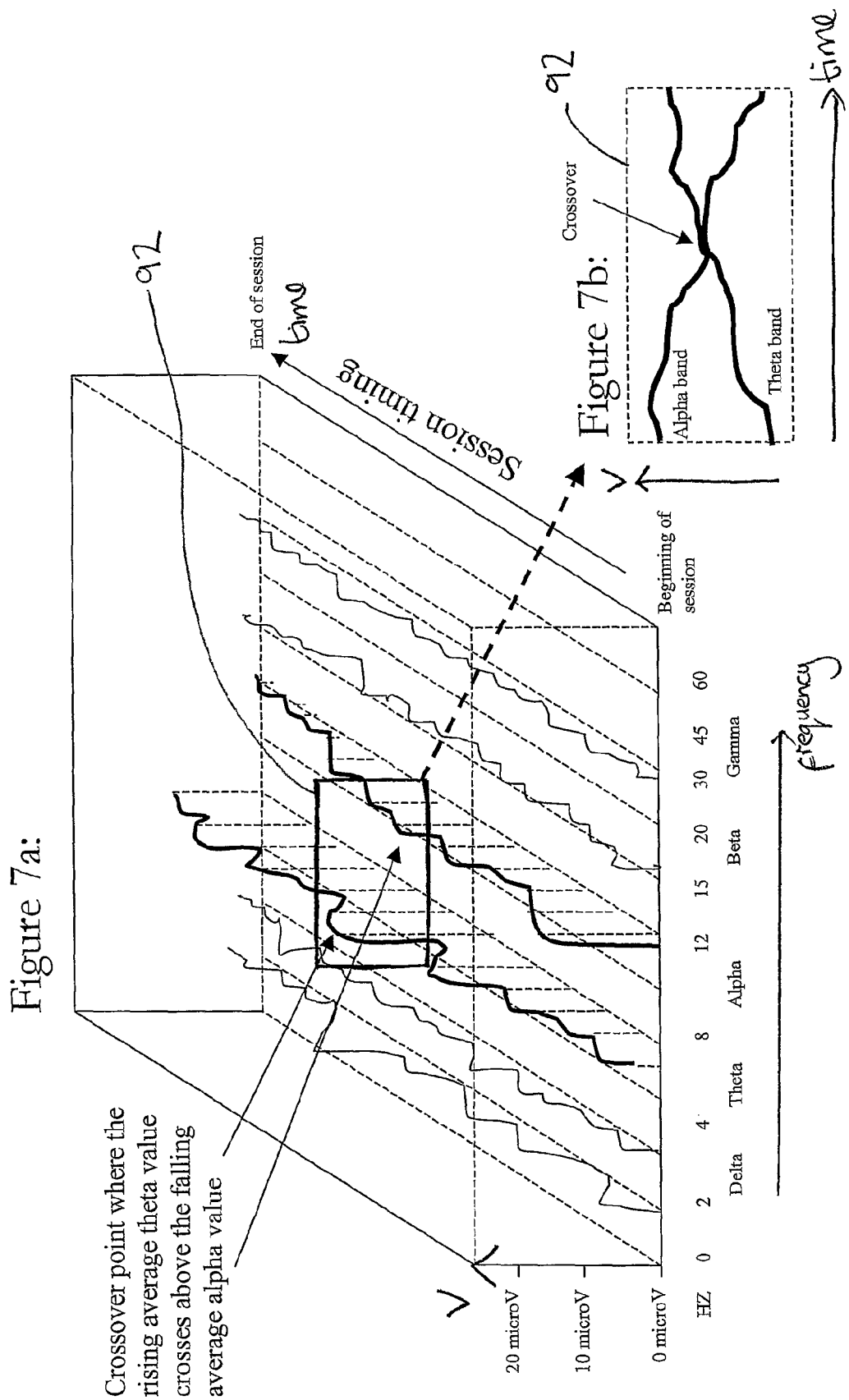

FIG. 7a is similar to the three-dimensional representation 90 of a complex multi-frequency brainwave signal of FIG. 6a, and references a section of time 92, during which alpha-theta cross-over occurs. The section of time 92, during which alpha-theta cross-over occurs, in FIG. 7a, is shown in FIG. 7b.

As shown in FIG. 7b, a waveform representative of the alpha frequency band near the beginning of the hypnosis session is relatively high, in comparison to a waveform representative of the theta frequency band.

As the session progresses, and as the user is being relaxed, the three-dimensional representation 90 of a complex multi-frequency brainwave signal shows that amplitude (power) the waveform representative of the alpha frequency band reduces as the amplitude of the waveform representative of the theta frequency band increases.

Figure 8:
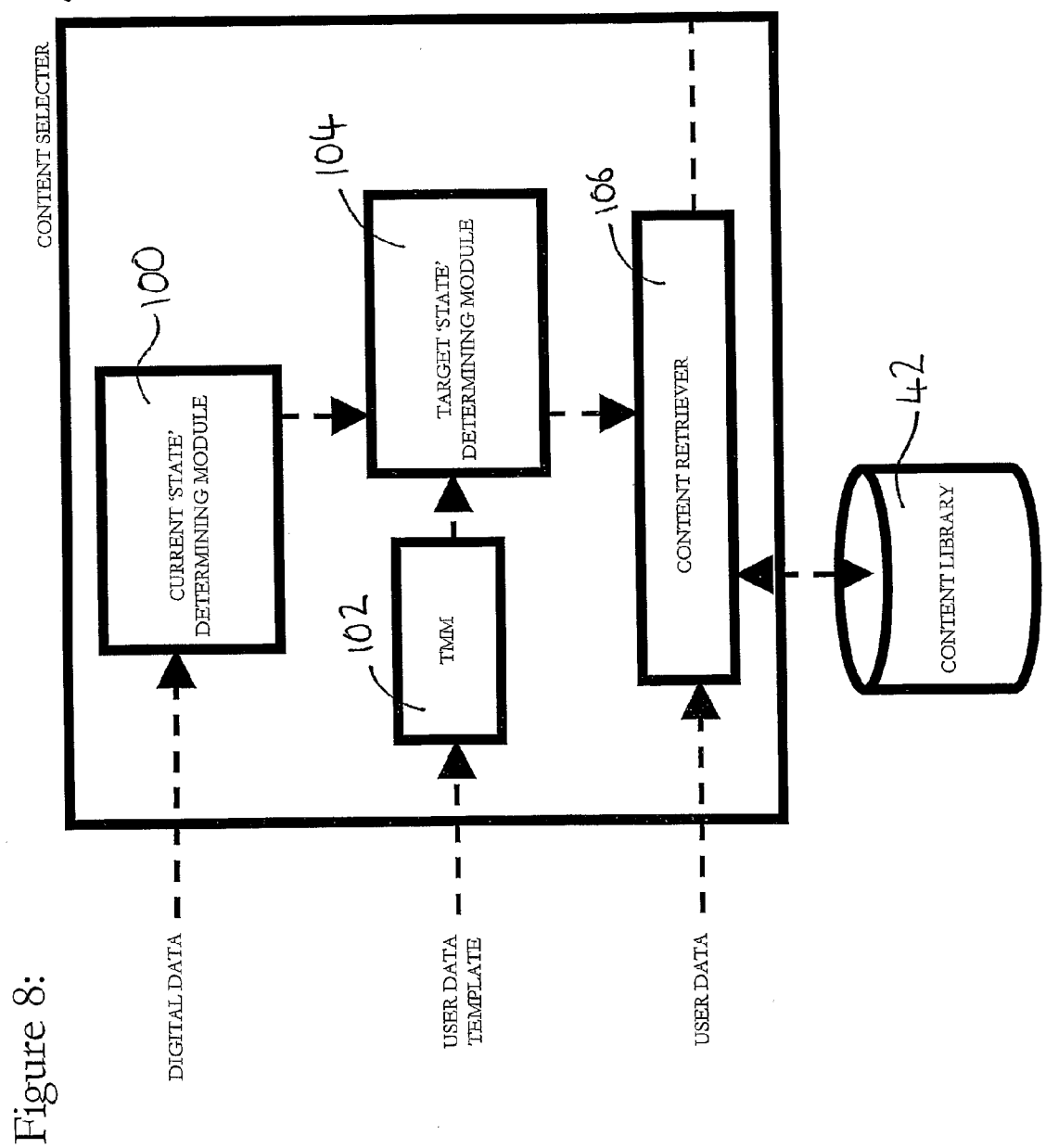
FIG. 8 is a schematic block diagram of the content selector of FIG. 5.

A functional block diagram of the content selector 76, which is arranged to select the most appropriate content clips, is shown in FIG. 8. Content clip selection may be carried out in real-time, just prior to the expiration of a currently playing clip.

As shown, the content selector 76 comprises a current state determining module 100, for assessing a user's current neurological state on the basis of the predominant band determined from the received sensor data; a time management module 102, for controlling the length of each phase of the hypnotic session on the basis of the time specified by the session configuration module; a target state determining module 104, for determining from the current neurological state of the user and the time management module 102 a target neurological state for the user, and a content retriever 106, for selecting content from the content library 42 on the basis of the target neurological state and the user data.

The user data may relate to user preferences which may be entered via the session configuration module 70 by the user or administrator. These preferences may include voice/narrator selection, length of experience, selection or avoidance of particular exercises, music, sounds, clips, pace, language. It is to be appreciated that other selection criteria may exist. Advantageously, a high degree of personalisation of the content to be played may have a positive affirming affect on the user as they feel more in control and this can enhance any placebo effect that could occur.

The user data may also include details (through a session questionnaire) regarding previous success rates of particular content which has been played to the user during previous hypnotic experiences. As described below, content played during a hypnosis experience is analysed so that a measure of that content's effectiveness at achieving a particular goal can be determined. For example, a clip of relaxation content which has been determined to be very effective at relaxing a user may be highlighted as being effective and may be referred to as such within the user data associated with that user.

Additionally, during set-up at stage S0 of FIG. 1, the user may be asked to complete a number of simple psychological, personal profile and/or hypnotic susceptibility tests. The objective of these tests is to gain a better understanding of the user and to enable the system to deliver much more tailored content, which is specific to that user's personality and character traits. This psychological understanding helps to further tailor content to be delivered during the hypnosis experience. An example of a conclusion derived from such tests may be an understanding that a particular user reacts better to language that contains visual descriptions ("you can see a beautiful bird singing")—whereas another may react better to descriptions that are in auditory language ("you can hear a beautiful bird singing"). The tests will be presented to the user on screen and via headphones while they are fully conscious and before the first ever induction for them has begun. The results of such tests will be stored in the user data section 54 of the database 40 for that user.

The current state determining module 100 determines the neurological state of the user on the basis of the sensor data signals from the signal processor 72 of FIG. 5. Starting from a known neurological state, (i.e. the start of each hypnosis experience the user is always in the alert state), the system may determine whether any changes in the neurological and physiological parameters are sufficient to indicate that the user's state has changed.

As described above the sensor data signals may originate from more than one type of sensor 32a, 32b, 32c, i.e. EEG, GSR and HRV. In one embodiment, the EEG signals may be used as the main indicator of neurological state and the GSR, HRV and other signals may be used to corroborate or confirm the neurological state indicated by the EEG signals. In this way the system will not indicate that the user's state has changed until the additional GSR, HRV and other signals fall within particular boundaries which are consistent with a change in neurological state of the user. It is to be appreciated that different weightings may be attributed to the readings from different sensors 32a, 32b, 32c.

The current state determining module 100 uses rules 62 stored in the rules section 60 of the database 40 to determine if the state of the user has changed.

The rules 62 typically have an IF <CONDITION> THEN <RESULT> format. The rules 62 may be specified in order of importance such that some rules are more critical than others. Alternatively, constraint-satisfaction techniques may be used. A simplified example set of rules is shown below.

```
IF< previous_state = alpha >
AND IF < power_of_theta ≧power_of_alpha >
AND IF < heart_rate is between A to B bps >
AND IF < HRV is in range C to D >
AND IF < GSR is in range E to F >
THEN < current_state = theta >
ELSE < current_state = previous_state = alpha >
```

In one embodiment of the invention, the device incorporates machine learning which enables the system to tailor the values of the boundaries of the neurological and/or physiological parameters (A to F above) for each user. This is discussed in more detail below.

The user's state when determined is output to the target state determining module 104.

The time management module (TMM) 102 monitors time throughout the hypnosis session. The TMM 102 uses the pre-defined length of the session, and the length of time expired throughout the session to assist in the evaluation of the most appropriate content clip to be played next.

Figure 9:
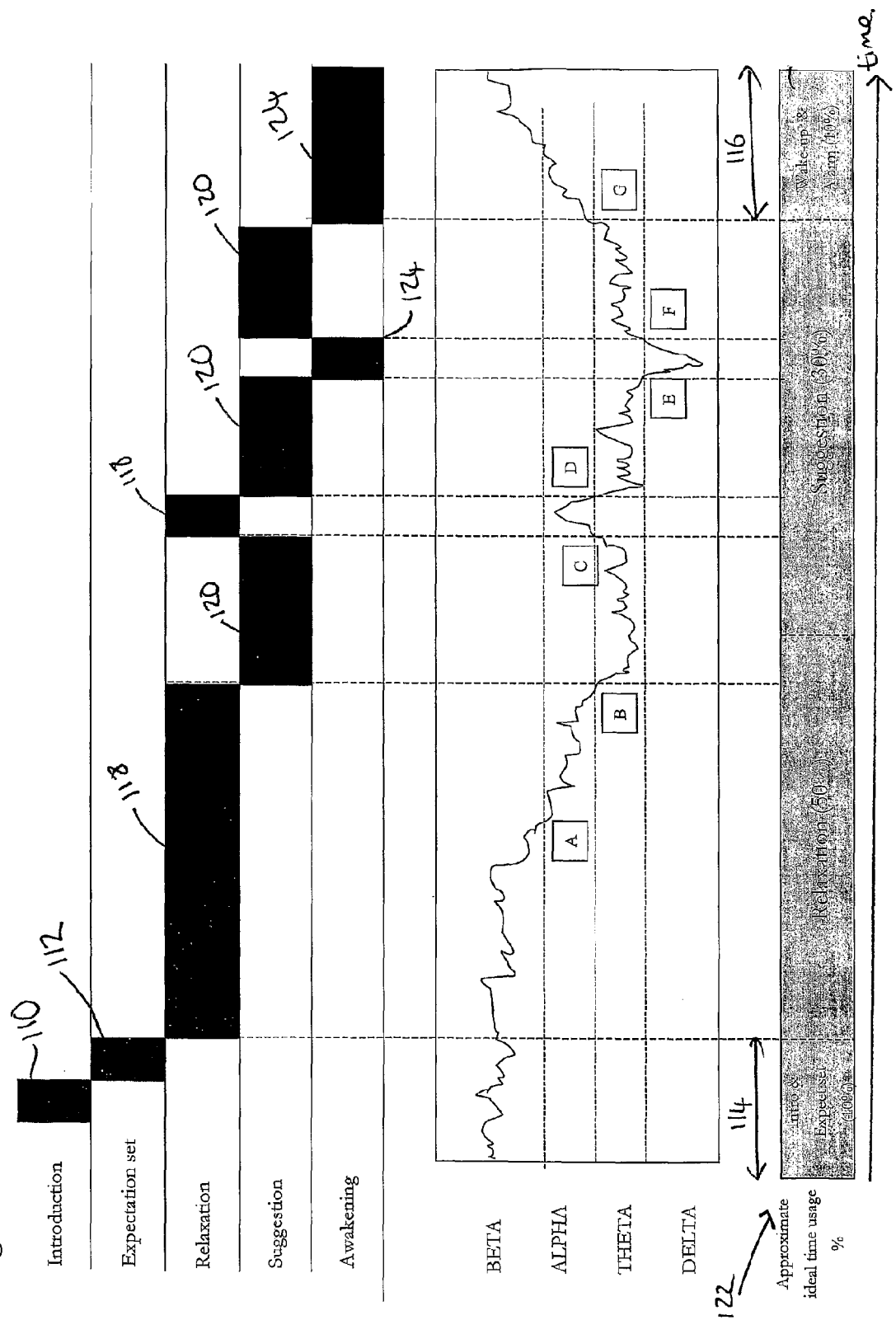
FIG. 9 is an example timeline of a hypnosis session showing the relationship between content delivery, predominate band-power and a timing guideline.

With reference to FIGS. 1 and 9, the timing of a hypnosis session is determined as follows. The set-up phase at stage S0 is typically not counted within the timing of the session as this involves the application of sensors 32a, 32b, 32c and testing to the user etc. The session timing, therefore, commences when the system is instructed to move to stage S1. During this stage, introduction and expectation content clips 110, 112 are played to the user. The timing 114 of this stage is typically fixed, and may account for approximately 10% of the overall session length.

In addition, the length time to wake up a user, including an alarm sound if necessary, may also be a fixed amount of time 116, and this may account for approximately another 10% of the overall session length.

Therefore, within the remaining 80% both relaxation content 118 and instructional/suggestive content 120 must be played. In one embodiment, the system may attempt to play relaxation content 118 for approximately 50% of the total time and instructional/suggestive content for the remaining 30%. These approximate timings act as a timeline guideline 122, however, actual content deliver is dependent on the timeline guideline 122 and the current neurological state of the user, i.e. the user may be in a suitably relaxed state before 60% of the time has expired. In which case, the content selector 76 will switch from providing further relaxation content 118 to delivering the instructional/suggestive content 120.

As such, the TMM 102 determines using the timeline guideline 122 for each hypnosis session an expected state for the user, i.e. the state the user is expected to be in at any particular time.

The target state determining module 104 is arranged to determine from the current state provided by the current state determining module 100 and the TMM 102, a target state for the user. For example, if the current state is relaxed awareness, and the expected state is relaxed awareness, the target state will be deeply relaxed since the user must be in this state before instructional/suggestive content 120 can be played. Conversely, if the current state is deeply relaxed and the expected state is relaxed awareness (i.e. the user has moved into the deeply relaxed state ahead of the approximated guideline time), the target state is deeply relaxed such that instructional/suggestive content 120 can be played at that time.

The target state determining module 104 determines, from the current state and the target state, the type of content to be played next, i.e. relaxation 118, instructional/suggestive 120, or wake-up content 124. This output may comprise the type of content to be played next (i.e. relaxation 118, such that the content retriever 106 is able to select the most appropriate content. The table below shows what the type of content should be depending on the current state and target state: the target state depending on the expected state at a particular time during the session.

| Current state | Target state | Type of content |
| --- | --- | --- |
| Alert | Deeply relaxed | Relaxation |
| Relaxed awareness | Deeply relaxed | Relaxation |
| Deeply relaxed | Deeply relaxed | Instructional/suggestive |
| Deep sleep | Deeply relaxed | Wake-up |
| Deeply relaxed | Alert | Wake-up |

In this manner, the device is responsive to the real-time feedback provided by the system rather than simply following a predefined timeline. Instructional/suggestive content 120 may be more effective the longer it is played to the user. Therefore, the system is optimised because it provides the best possible content at any given time.

A diagram showing the relationship between content delivery, predominate band-power and timing guideline is shown in FIG. 9. As shown, introduction 110 and expectation content 112 are played to the user while they are still in the alert state. As relaxation content 118 is played, the predominant beta band-power reduces until the alpha frequency band becomes the predominant band at time A. The alpha band-power reduces until the alpha-theta cross-over point at time B.

At this time, the relaxation content 118 is replaced with suggestive/instructional content 120 until time C, where the system detects that the predominant band has reverted to the alpha frequency band. At this time, further relaxation content is played to the user until the predominant band crosses over again to the theta band, at time D.

Suggestive/instructional content 120 is resumed until time E, where the system detects that the predominant band switches to the delta band, indicating that the user is too relaxed such that they are in the deep sleep state. At this time, wake-up content 124 is played to the user to bring them out of the deep sleep state and back into the deeply relaxed state at time F, where suggestive/instructional content 120 is once more resumed.

Suggestive/instructional content 120 continues to be played until the system, at time G, determines that the session time is soon to expire. As a result, the system plays more wake-up content 124, which may also include an alarm sound, until the user wakes up, as shown by the return of the predominant power-band to beta.

As shown in FIG. 9, the user initially entered the deeply relaxed state ahead of the approximate time (i.e. after 60% of the total session time). This is because the system is responsive to the feedback from the user indicating that the user was in the target deeply relaxed state.

The content retriever 106, on the basis of the content type output by the target state determining module 104, is arranged to select the most appropriate clip of that content type from the content library 42.

Figure 10:
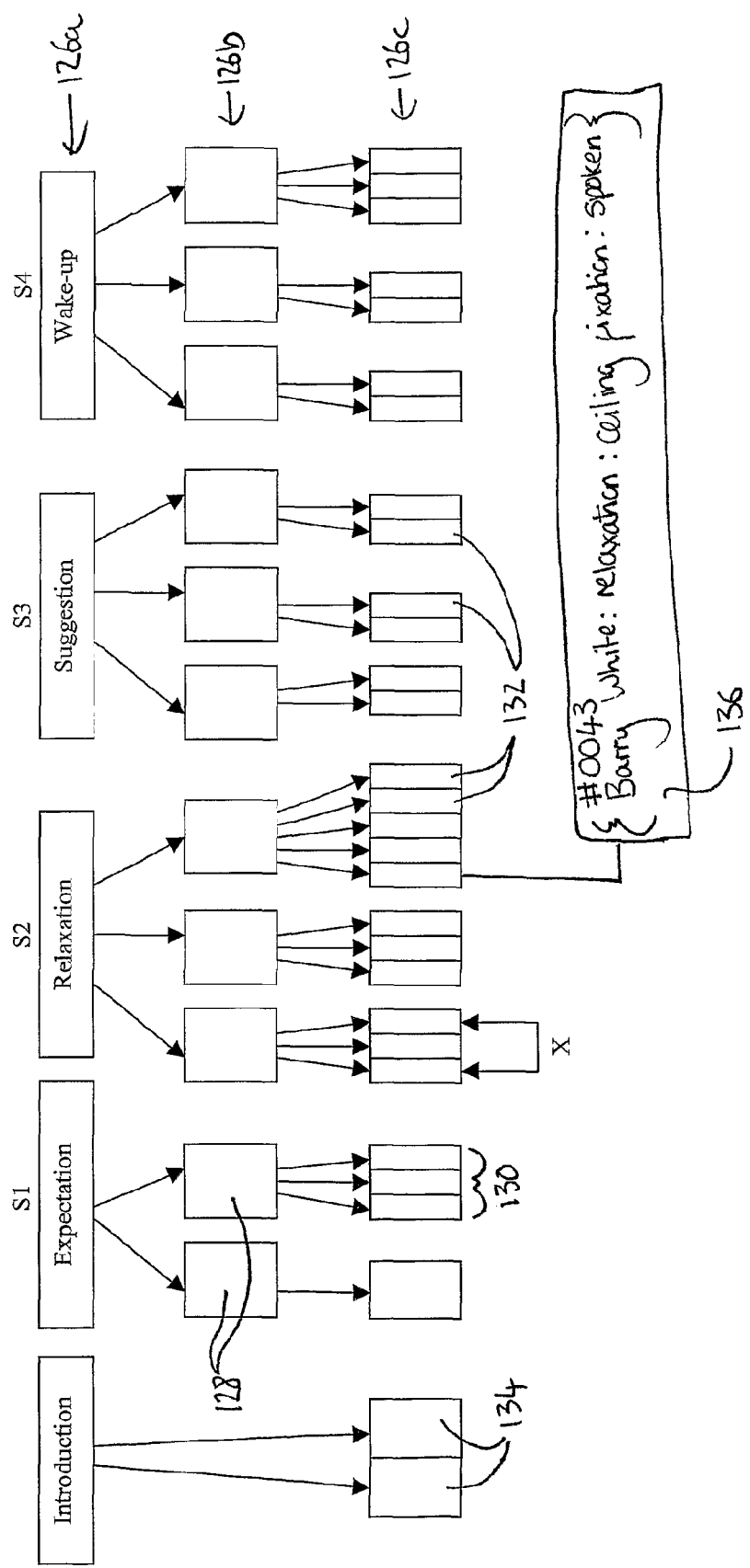
FIG. 10 is a schematic diagram of a content hierarchy showing organisation of a plurality of content clips by section and content type.

In one embodiment, clips of content may be organised as shown in FIG. 10. As shown, there are typically three levels 126a, 126b, 126c in a content hierarchy. At the highest level 126a, the content is categorised into content types (i.e. relaxation, suggestion, etc.) relating to the stage of the induction (i.e. stage S2, stage S3 etc.) shown in FIG. 1.

Each content type may be further divided into sections and/or sub-sections 128, representing a group of commonly linked content clips 130, which are shown at the lowest level 126c of the content hierarchy. Content clips may be grouped in a number of different ways.

Typically, there may be more than one introduction clip, however, each introduction clip 134 stands on it's own and simply includes introductory content and instructions (for example what to do if the fire alarm sounds). As such, introduction content may not be divided into sections.

Expectation content may be sectioned into a standard expectation message section (i.e. "so, get ready to relax, now, enjoy and . . . ") and a tailored message section ("improve your golf, tennis, energy levels etc).

Relaxation content clips may be grouped in relation to a particular technique or exercise. For example, a section of relaxation clips may be related to a ceiling fixation technique which is designed to focus attention on a particular place on the ceiling.

In addition, each content clip 132 in FIG. 10, will typically be recorded by a plurality of different narrators (voice artists), in order to facilitate user selection of a narrator of choice. Narrators are chosen for the relaxing, resonant quality and tone of their voice. Each narrator may record all or some of the inductions, content clips of which are stored in the content library within the database. By listening to short clips of a range of voices the first time they use the system, a user can pick the voice they enjoy the most. This self selection is also applied to other sound clips such as music selection or desired relaxation sounds. Finally, if required the user can also self select their own induction content clips, choosing to repeat and/or remove certain pieces of content that they wish.

The content clips 132 may be stored as individual audio/visual files or other types of stimulus files. The format of audio/visual files may be media player 3 (mp3) files or other suitable voice, sound and visual media/audio formats.

Virtual reality technologies may be utilised to provide a connection between aural statements played to the user and visual representations of those statements, i.e. visual representations of a user achieving their goals may be generated and displayed to the user.

Organising the content clips 132 in this manner enables the content clips to be tagged with metadata 136. Such metadata may include content clip number, narrator, content type, content type section, content type sub-section, spoken text, background music, and sound effects. It is to be appreciated other metadata categories may exist.

For example, a clip may be tagged with the following information:
Content clip #0043: {Barry White, relaxation, ceiling fixation, spoken text}

Tagging clips in this manner enables the content retriever 106 to select appropriate content clips 132 from the clips available, and further enables the selected clips to be retrieved from the content library 42, concatenated with other appropriate clips such that a continuous stream of content is played to the user as required.

Each content clip 136 can be combined in different ways or with other material to produce a wide variety of different hypnosis experiences. However, some of the content clips 136 have a very specific relationship (see reference X in FIG. 10) to other clips. For example, some clips may be tagged to ensure that they are only ever played after certain other clips (in the case of a sequence of clips within a section). Likewise other clips may be tagged to ensure they are always played before other clips.

Content selection rules define which content clip is to be played next on the basis of one or more of the following content selection criteria: the content type, determined by the target state determining means; content attributes, defined by metadata 136; a session history of which clips have previously been played, including relationships between the content previously played and other content clips and the number of times a content clip has been played. The content selection rules may also relate to what is being played via another channel, for example a rule may indicate that a particular content clip of background music may only be played if the speech content being played has certain characteristics (defined by metadata 136).

The format of each content selection rule may follow that of the current state determining rules described above. A simplified example rule is shown below.

```
IF< content type = relaxation >
AND IF < content_section = ceiling fixation >
AND IF < ceiling fixation content clip # 1 is playing >
```

-continued

```
AND IF < # of times played < 3 >
THEN < next_content_clip = ceiling fixation content clip # 1 >
ELSE < next_content_clip = ceiling fixation content clip # 2 >
```

In addition to determining the most appropriate content clip to be played on the basis of the above content selection criteria, the content selection rules may also be adapted for each hypnosis session to account for user specified preferences regarding, for example which narrator to use, which content to use or avoid, and the language of the content to be played. In addition, the user specified preferences may include an indication of which content to use on the basis of a psychological test or profile taken by the user, i.e. visual versus auditory relaxation techniques.

Examples of content clips are shown in the table below.

| Type of content | Section | Example content clip |
|---|---|---|
| Expectation | Choice to exit | Remember too that if any sudden problem should arise, anything important that needed your attention, you would be back to normal instantly. |
| Expectation | It's only sleep | During this session you will be relaxed and you may feel like you are not aware of time. Some people drift into light sleep, which is fine and still very effective. At the end of the session you will either hear the instructions to awaken or after a few more minutes, a wake up . . . |
| Expectation | Get ready | So, get ready to relax, now, enjoy and [Message: improve your 1] |
| Relaxation | Comfy position | Now sit back and make yourself comfortable feet flat on the floor and arms comfortably at your side. |
| Relaxation | Ceiling fixation | Look directly up above your head and see if you can find an area on the ceiling or on the wall to comfortably fix your gaze on. Then move your eyes up to a spot on the ceiling perhaps eight or ten inches above that comfortable point. A spot or a pattern on the paper or even a plaster crack will do nicely. Now when you look at it, the position of your head will be relaxed but your eyes will have to make a very slight effort to look up at the spot. Sit back completely comfortably and relaxed. Now . . . Focus your eyes on the spot you've chosen and start to relax very thoroughly, very deeply and very . . . |
| Relaxation | 10 to 1 count | As I count. 10. 9. 8. Feel yourself going down and down, deeper and deeper down. 7. 6. 5. Going further and further down, deeper and deeper down. Your eyelids heavy and drooping and closing. They can close any time they want to now. Close any time they want to, and go deeper and deeper relaxed. 4. 3. 2. 1. 0. Go deeply down . . . |

The hypnosis device, in one embodiment, also comprises a session recording and analysis module 78, which takes as inputs a recording of the stimulus provided by the stimulus output module 24 and the input signals from the sensors 32*a*, 32*b*, 32*c* (typically after signal processing). Both inputs are recorded synchronously as session data, such that neurological and physiological feedback from the user correlates in time with the stimulus causing the neurological and physiological feedback, albeit there will be some delay between a particular event causing a particular neurological and physiological feedback result.

In one embodiment, as each content clip 132 is played, it may be time-stamped in relation to the overall time progression of the hypnosis session. This permits later analysis of the content played and it's degree of success based on measured neurological and physiological responses.

The session data is recorded in the session results section 56 of the database 40 to enable analysis to be performed on the session data. This analysis enables the system to use machine learning to improve session results. Analysis of the session data may be carried out as the session is progressing and/or after the session has finished.

Typically, the session results are stored in session templates. A template is a collection of rules defining a session. Administrators are able to use templates to easily specify sessions for new subjects.

In addition, other inputs into the learning process could be from the user's profile, other user's results or from additional analysis. Based on the results of any analysis, the system is able to automatically add rules, preferences and/or adjust thresholds.

For example, the system may detect that there is a statistically significant correlation between playing a certain clip and the user drifting out of the deeply relaxed (susceptible) state. In such a case the system may automatically add a rule that specifies not to play that clip to that user. Similarly, the system may automatically detect induction clips that are more effective than others, either for a specific user or for the vast majority of users. Analysis techniques are expected to be known to a personal skilled in the art and further description is not required here.

Another input into the learning process may be answers to a session questionnaire provided to the user at the end of a hypnosis session. Answers to questions about the session may provide useful insight into the effectiveness of certain content which may otherwise not be captured or used to amend the rules governing what content should be used.

It is to be expected that the more a particular user uses the system, the more adept the system will be at delivering the most appropriate content at the right time.

The system is also arranged to offer specific content delivery techniques, such as binaural beats, double induction, and subliminal messaging.

Binaural beats comprises presenting individual tones to each ear of a user. If one ear is presented with a steady tone of say 500 Hz and the other ear a steady tone of 510 Hz, these two tones combine in the brain. The difference, 10 Hz, is perceived by the brain and is a very effective stimulus for brainwave entrainment. (Effectively the brain begins to 'resonate' at the entrained level of Hz). This 10 Hz is formed entirely by the brain. When using stereo headphones, the left and right sounds do not mix together until in your brain. The frequency difference, when perceived by brain this way, is called a binaural beat. This means that you can artificially drive the brain to a desired state (eg Theta at 4 to 7 Hz) if required or if the system user is not exhibiting this state.

Double induction involves playing two messages, at the same time, to a separate ears. The principle is that the conscious mind tries to listen to one message, while the other goes directly into the subconscious mind, by-passing the conscious filter.

Subliminal messaging requires that very rapid messages or words are played, to the user, so fast that the conscious mind does not 'register' or filter them. The unconscious mind however recognises the messages/word and the suggestions are embedded. This technique also works with visual content.

As described above, alpha-theta crossover is not the only way of determining whether the user's state has changed to being susceptible to instructions or suggestions, as other techniques may be used in combination with the alpha-theta cross-over indicator (i.e. to corroborate results) or on their own.

An event-related potential (ERP) is a electrophysiological response to a stimulus. More simply, it is a measured brainwave response caused as a direct result of a thought or perception. ERP's give an indication of many of the features associated with hypnotic state such as an assessment of focused attention, inattention to extraneous stimuli and absorption.

ERPs can be reliably measured using EEG. However, because the brain simultaneously carries out thousands of ongoing processes, it is unlikely that an EEG reading will be able to identify a response to a particular stimulus. As such, it is difficult to see an ERP after the presentation of a single stimulus. A most robust method relies on monitoring responses after many dozens or hundreds of individual presentations, and averaging together the responses. This technique cancels out noise in the data enabling detection of the voltage response to the stimulus.

Figure 11:
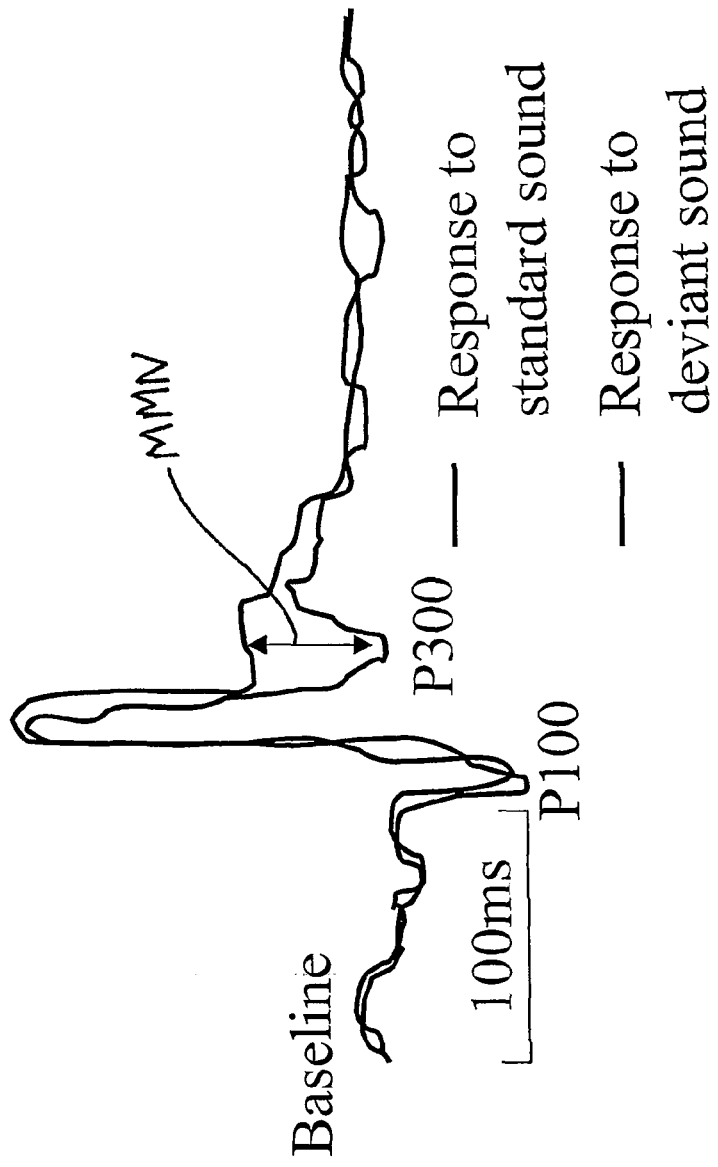
FIG. 11 is an example waveform of a brainwave response to a standard and deviant sound.

Two components of the ERP which are of special importance to stimulus evaluation, selective attention, and conscious discrimination in humans are the P300 positivity and N200 negativity, appearing, as shown in FIG. 11, 300 ms and 200 ms post-stimulus, respectively.

One of the most robust features of the ERP response is a response to unpredictable stimuli. This response, known as the P300 (or simply "P3"), manifests as a positive deflection in voltage approximately 300 milliseconds after the stimulus is presented.

Mismatch negativity (MMN) is a change-related brain response or neurophysiological index. It is an auditory event-related potential (ERP) component relating to the N200 and P300, which is elicited task-independently by the detection of an infrequent change in a repetitive sound sequence. The Mismatch Negativity can be elicited in the absence of focussed attention.

MMN is calculated by subtracting ERPs to the standard stimuli from ERPs to the deviant stimuli across the 2 instances of N200 and P300. This negative wave has been suggested to reflect the function of an automatic preconscious detector of stimulus change and attention.

In some studies, the neural mechanisms associated with hypnosis have been investigated in a single highly hypnotisable subject by measuring the mismatch negativity (MMN) component of auditory ERP, in normal baseline state and under hypnosis. Some findings indicate that the frontal inhibition associated with hypnosis can be measured as a decrease in MMN. In hypnosis the MMN was significantly larger compared to baseline. This was in contrast to low hypnotizable subjects where an opposite pattern of change was found.

Figure 12:
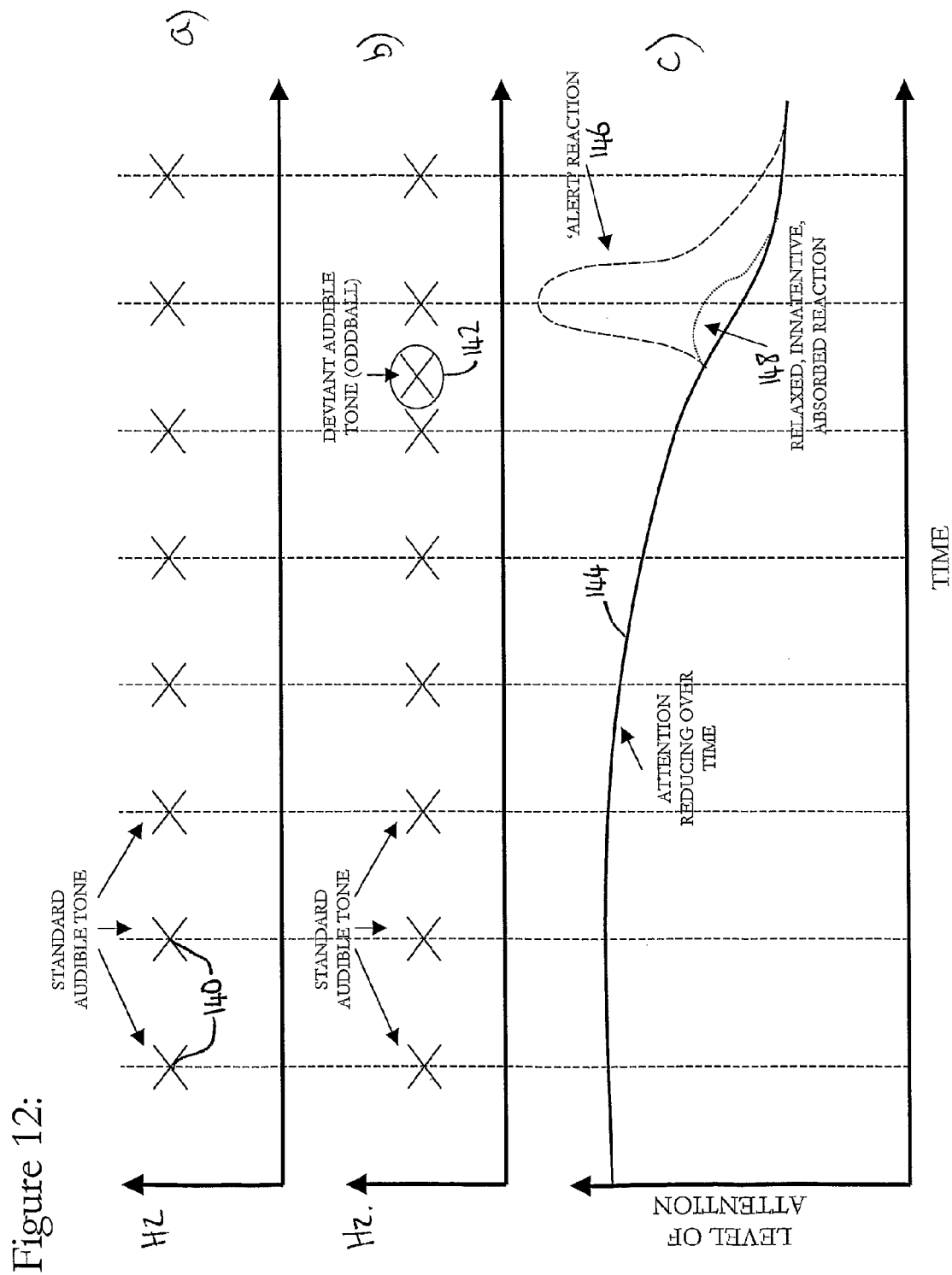
FIG. 12a is a timeline of standard audible tones played to a user.
FIG. 12b is a timeline similar to FIG. 12a including the standard tones of that diagram and a deviant 'oddball' tone.
FIG. 12c is an example graph of attention versus time representing a user's level of attention (i) when the tones of FIG. 12a are played, (ii) when the tones of FIG. 12b are played while the user is 'alert', and (iii) when the tones of FIG. 12b are played while the user is in a 'deeply relaxed' state.

FIG. 12a shows a timeline of audible tones 140 which are played to the user. These tones 140 are played at fixed intervals and it is to be expected that over time, the user's attention to these tones will drop since typically the human brain filters them out. FIG. 12b shows a timeline similar to that of FIG. 12a. As shown, a deviant sound 142 is introduced between two standard tones 140 known as an 'oddball' tone. When a user is in an alert state, the brain will 'pick-up' this sound as being out of the ordinary and as a result an ERP response can be measured. This exercise provides a good gauge on the level of a person attention.

FIG. 12c shows a user's attention levels as they are listening to the tones of FIGS. 12a and 12b. The continuous line 144 shows a user's attention dropping off as they are listening to the tones of FIG. 12a. The long-dashed line 146 relates to a user in an alert state, listening to the tones of FIG. 12b, and shows a sharp peak in the user's attention at the time that the deviant tone plays. This is to be expected as an alert user will consciously notice the change in the timings of the tones.

However, a user in a deeply relaxed state will show a response like that of the dotted line 148 in FIG. 12c, when listening to the tones of FIG. 12b.

By calculating the MMN as described above, the system is able to determine a user's level of attention and this can also be used as an indicator of the user's level of relaxation or susceptibility to instructions or suggestions.

It may be desirable to find out the origins of individual signals which have been mixed together (i.e. different signals from different areas of the brain being picked up by one sensor). One way this may be achieved is through independent component analysis (ICA). This is a mathematical/computational method for separating a signal that is multivariate into its various components achieved by assuming that several factors are true.

The classical analogy is the "cocktail party problem", where a number of people are talking simultaneously in a room, and one is trying to follow one of the discussions. Imagining that there are microphones around the room to capture all speech, ICA using a statistical analysis algorithm, allows separation of the underlying desired speech signals from the sample data consisting of people talking simultaneously.

Although there are several challenges and issues with applying this technique to real world data many examples have shown that ICA can extract EEG activations and isolate certain artifacts (such as line noise, eye blinks, and cardiac noise). Used in combination with functional magnetic resonance imaging (fMRI) scientists have been able to make a number of discoveries about the how the brain operates using widely held assumptions about neural mechanisms.

By separating event related potential (ERP) data into a number of components, ICA reveals EEG activity that is robust, reliably time-locked and phase-locked to events used in experiments and this reduces the need to average results across multiple ERP trials. As such this technique may enable single trial recognition of ERP stimulus. This method of ERP analysis can be used to compare responses from multiple stimuli, task conditions, and subject states. It can also be used for tracking a number of states such as alertness.

ICA can be used in combination with ERP (N200, P300, MMN) to determine a measurable hypnotic signature or indicator, in real time analysis. This, in combination with other indicators (such as alpha-theta cross-over), can be used to trigger and drive different content types in accordance with the present invention.

Using motion sensors, the system may be able to recognise when the user moves certain parts of their body, i.e. in response to certain instructions which are given and that require the monitoring of movement. For example, if the user hears an instruction to move one of their fingers, the motion sensor detects such a movement. This movement would be automatically registered by the system as a positive response to that suggestion. Examples of instructions which would provide a useful response include providing an instruction that states that the user cannot move a particular finger, or that they are to imagine that a balloon is tied to the user's hand. Movement of the finger in the first example implies that the user is not in a susceptible state because if they were they would believe that they couldn't move that finger (i.e. their subconscious mind would follow the instruction). Movement of the hand in the second example indicates that the user is in the susceptible state and their imagination is causing them to follow the instruction.

Further indicators which may be used to assist in the determination of user neurological state include increased theta wave activity (particularly in the frontal regions), decreased alpha wave activity, increased 40 Hz gamma wave activity, higher alpha wave activity in the posterior cortex, and/or the combination of high theta wave activity and low alpha wave activity.

In general, prior to a user's first hypnosis session, a default susceptibility state will be defined and used as a target state for delivery of the instructional/suggestive content. An example target state could be indicated on the basis of alpha/theta crossover. When this specific brainwave pattern is recognised, the system begins to deliver the instructional/suggestive content for a specified subject. This target state reference and default setting will remain central to the systems objectives until 1) research suggests otherwise 2) a genuine identifiable hypnotic signature is found or 3) use of the tool provides evidence to suggest other measurements should be used for that individual. Within the defined system, target state parameters are adjustable to allow research and personal tailoring. The present invention may also be adjusted to monitor for and locate a specific hypnotic signature if pre-defined. It is also quite possible that the present invention will assist in finding and defining the elusive 'hypnotic signature'.

It is to be appreciated that some sensors may comprise built-in ADCs or other signal processing capabilities, i.e. noise filtering or amplification. However, according to one embodiment of the invention the hypnosis device itself provides for ADC.

The invention as described above refers to a dedicated device including the necessary sensors, display and speakers/headphones. However, it is to be appreciated that the present invention could also be carried out utilising existing hardware such as personal computers, game consoles, such as Sony's Playstation® and, Microsoft's Xbox®, and personal MP3 players. In the case of using a games console, it would be relatively easy to provide a visual as well as an auditory stimulus to a user, using the television screen or computer monitor. Other types of stimulus may be used. For example, anything that helps relax the human mind by influencing the senses i.e. touch—using a massage device, smell—using aromatherapy, or even taste.

Furthermore, it is to be appreciated that the present invention need not be limited to the various sensors described herein. Any sensor, which detects a human body physiological parameter, which can be correlated to a state of the human mind and body, can be used, in combination with other sensors or by itself. For example, a sensor to detect the blood/oxygen level, a video camera to monitor movement, pressure sensors etc.

In addition, the list of goals discussed above is not exhaustive. It is to be appreciated that a broader range of users are offered, for example, a variety of obscure health issues (phobias etc) and less well known sports or specific performance users. Inductions can even be tailor-made to an individual's goal. The present invention need not be limited to the specific goals discussed herein.

It is to be appreciated the present invention may also detect and monitor other brainwave outputs.

It is also to be appreciated that the database need not be stored locally within the hypnosis device itself. The hypnosis device may be provided with access to a centrally stored database, accessed via the internet. A centrally stored database may be provided in addition to a locally stored database.

In addition, it is to be appreciated that the stimulus output module and the sensor data receiver need not be contained within the hypnotic device. In particular, the processor may be a central server which is accessed via the internet. In this way a user may access and interact with a website which provides access to a hypnosis session service. In this case, the user's local PC provides the output stimulus module and the user's PC in use takes inputs from sensors, and transmits the sensor data to the central server for processing.

It will be understood that the embodiments described above are given by way of example only and are not intended to limit the invention, the scope of which is determined by the appended claims. It will also be understood that the features described in one embodiment may individually or collectively be used in other embodiments.

The invention claimed is:

1. A hypnosis device for controlling administration of a hypnosis experience to a user, the hypnosis device comprising:
 a stimulus output module for outputting a first type of content via one or more media channels to one or more sensory output devices for presentation to the user;
 a sensor data receiver for receiving feedback data comprising electrical activity data representative of brainwave activity of the user, the brainwave activity of the user being measured using a technique which comprises electroencephalography (EEG),
 an electronic processor configured to normalize the electrical activity data into an index value and to determine in substantially real-time that the index value of the normalized electrical activity data is within a threshold range,
 the electronic processor is configured to generate instructions for the stimulus output module to output a second type of content based on detecting the index value is within the threshold range,
 the electronic processor is configured to generate instructions for the stimulus output module to output the first type of content based on detecting the index value is outside the threshold range,
 the threshold range indicates that the user is in a trance state to receive the second type of content, the trance state indicating that the user is in a state of absorbed, focused and attentive neurological state,
 the first type of content is configured to relax and put the user in an absorbed, focused and attentive neurological state for receiving the second type of content; the second type of content is configured to provide the user with instructional content; and
 an electronic memory for storing the first and second types of content.

2. The hypnosis device as claimed in claim 1, further comprising a brainwave sensor, the brainwave sensor being arranged to measure the brainwave activity of the user.

3. The hypnosis device as claimed in claim 1, further comprising a physiological parameter sensor arranged to measure a physiological parameter of the user.

4. The hypnosis device as claimed in claim 3, wherein the physiological parameter sensor is arranged to measure a physiological parameter which is one of a group comprising galvanic skin response, heart rate variability, and rate of breathing.

5. The hypnosis device as claimed in claim 3, wherein the hypnosis device comprises a plurality of different physiological parameter sensors measuring a plurality of different physiological parameters simultaneously.

6. The hypnosis device as claimed in claim 3, wherein the electronic processor comprises a current state determining module for determining a current neurological state of the user using the received feedback data.

7. The hypnosis device as claimed in claim 6, wherein the current state determining module is configured to determine the current neurological state of the user by corroborating the received feedback data from a brainwave sensor with the physiological parameter from the physiological parameter sensor.

8. The hypnosis device as claimed in claim 3, wherein the stimulus output module is arranged to output movement instructions and the physiological parameter sensor comprises a motion sensor.

9. The hypnosis device as claimed in claim 1, wherein the received feedback data comprises a complex multiple frequency signal, and the electronic processor is arranged to determine a predominant frequency signal from the complex multiple frequency signal.

10. The hypnosis device as claimed in claim 9, wherein the predominant frequency is within one of a plurality of frequency bands and wherein the electronic processor is arranged to detect a change in a neurological state of the user at a point in time when the predominant frequency changes from being in one frequency band to being in another frequency band.

11. The hypnosis device as claimed in claim 1, wherein the first and second types of content is an output signal that comprises an audio signal or a display signal.

12. The hypnosis device as claimed in claim 11, wherein the feedback data drives both a selection of content and a visual display device that generates a visual representation of the user's brainwave activity which helps the user to achieve a particular goal.

13. The hypnosis device as claimed in claim 11, wherein first and second types of content is a display signal for driving a visual display device to generate a virtual reality representation of the user achieving a particular goal.

14. The hypnosis device as claimed in claim 13, wherein the stimulus output module is arranged to output a stereo audio signal, comprising a first audio signal for presentation to a first ear of the user and a second audio signal for presentation to a second ear of the user, the first audio signal comprising a first frequency signal and the second audio signal comprising a second frequency signal, wherein the first and second frequency signals are selected for provision of a binaural beat audio signal.

15. The hypnosis device as claimed in claim 13, wherein the stimulus output module is arranged to output a stereo audio signal comprising a first audio signal for presentation to a first ear of the user and a second audio signal for presentation to a second ear of the user, wherein the second audio signal is a delayed version of the first audio signal.

16. The hypnosis device as claimed in claim 15, wherein the second audio signal has a greater amplitude than the first audio signal.

17. The hypnosis device as claimed in claim 1, wherein first and second types of content is an output signal for driving a device which stimulates the user's smell, taste or touch senses.

18. The hypnosis device as claimed in claim 1, further comprising a content selector for selecting the content to be output by the stimulus output module from a plurality of stored content data segments.

19. The hypnosis device as claimed in claim 18, wherein the content selector is arranged to execute a content selection rule to determine whether a selected segment can be outputted sequentially before or after another segment.

20. The hypnosis device as claimed in claim 19, wherein the content selector is arranged to prevent the selected segment from being outputted if the content selection rule determines that the selected segment should not be outputted.

21. The hypnosis device as claimed in claim 18, wherein each content data segment comprises at least one metadata tag describing attributes of the content data segment and the content selector is arranged to select content data segments using the at least one metadata tag.

22. The hypnosis device as claimed in claim 21, wherein the at least one metadata tag is arranged to specify one or more of the following content description items: content segment number, content narrator, content type, and content sub type.

23. The hypnosis device as claimed in claim 18, wherein the content selector further comprises a text-to-speech engine arranged to select text content from a plurality of stored text content data segments and convert the text content data segments into an audio speech signal to be outputted by the stimulus output module.

24. The hypnosis device as claimed in claim 18, further comprising the sensor data receiver for receiving text content data from an administrator, wherein the content selector further comprises a text-to speech engine arranged to convert the text content data into an audio speech signal to be output by the stimulus output module.

25. The hypnosis device as claimed in claim 18, wherein the hypnosis device is arranged to control a hypnosis session comprised of a plurality of sequential experience stages, the hypnosis session including an introductory stage, a relaxation stage, an induction/suggestion/instruction stage, and an awakening stage, each stage relating to a current neurological state of the user as the hypnosis session progresses.

26. The hypnosis device as claimed in claim 21, wherein the plurality of sequential experience stages includes an attention focusing stage which relates to a current neurological state of the user as the hypnosis session progresses.

27. The hypnosis device as claimed in claim 18, wherein the content selector is arranged to select a most appropriate data segment to be outputted by the stimulus output module based on a detected neurological state of the user, a current stage of a hypnosis session, and a desired subsequent stage of the hypnosis session.

28. The hypnosis device as claimed in claim 27, wherein the content selector is arranged to determine a next segment to be selected for output on the based on one or more of the following criteria: a content type, content attributes, a session history of which segments have previously been output.

29. The hypnosis device as claimed in claim 18, further comprising a time management module arranged to determine from a desired length of time of a hypnosis session and an expired time, a length of time remaining for the hypnosis session, wherein the content selector is arranged to select most appropriate data segments in accordance with the length of time remaining for the hypnosis session.

30. The hypnosis device as claimed in claim 18, wherein the content selector is arranged to enable an administrator to select content data segments.

31. The hypnosis device as claimed in claim 18, wherein the hypnosis device is arranged to receive user-specified preferences regarding data selection and the content selector is arranged to select content data segments in accordance with the user-specified preferences.

32. The hypnosis device as claimed in claim 18, further comprising:
a learning means arranged to learn using the feedback data which content data segments, after the content data segments have been outputted to the user, are most effective content data segments for encouraging the user to progress through a current stage of the hypnosis session; and
a data store for storing the most effective content data segments in a database record associated with the user.

33. The hypnosis device as claimed in claim 18, further comprising:
a profiling means arranged to administer a profiling test to the user prior to the hypnosis experience; and
a result determining means arranged to determine results from the profiling test; wherein the content selector is arranged to select most effective content data segments for encouraging the user to progress through different stages of a hypnosis session.

34. The hypnosis device as claimed in claim 33, further comprising a profile result storing means for storing the profile test results, and the most effective content data segments in a database record associated with the user.

35. The hypnosis device as claimed in claim 33, further comprising a means for determining baseline readings for the user, the baseline readings being representative of physiological readings obtained by the hypnosis device when the user is in an alert neurological state without being provided with a stimulus, and for using stored baseline readings for comparison during a hypnosis session.

36. The hypnosis device as claimed in claim 35, wherein the feedback data has a plurality of frequency bands and the hypnosis device further comprise means for determining upper and lower thresholds for each frequency band in order to determine specific thresholds which are personalised for the user for each frequency band.

37. The hypnosis device as claimed in claim 1, further comprising a session recorder arranged to record all activity within a hypnosis session to provide a full audit trail of every session.

38. The hypnosis device as claimed in claim 1, further comprising a real-time monitoring means arranged to monitor progression of the user through the hypnosis experience in real-time.

39. The hypnosis device as claimed in claim 38, wherein the real-time monitoring means includes a feedback channel including a microphone arranged to enable an administrator to output content to the user verbally during a hypnosis session.

40. The hypnosis device as claimed in claim 38, wherein the real-time monitoring means comprises a display for displaying a graphical representation of content output to the one or more sensory output devices.

41. The hypnosis device as claimed in claim 1, further comprising means for downloading content or an application for configuring the hypnosis device from a remote source via the internet.

42. A games console configured to operate as a hypnosis device according to claim 1.

43. The hypnosis device as claimed in claim 1 in combination with a sensory output device for presenting content to a user.

44. The hypnosis device as claimed in claim 1, wherein the electronic processor comprises state determining means for determining a current neurological state of the user using the received feedback data.

45. The hypnosis device as claimed in claim 1, wherein the hypnosis device is a medical device used in treatment of a medical condition.

46. The hypnosis device as claimed in claim 1, wherein the sensor data receiver is also arranged to receive physiological feedback data of the user from a physiological parameter sensor.

47. A hypnosis device for controlling administration of a hypnosis experience to a user, the hypnosis device comprising:

a stimulus output for outputting a first type of content via one or more media channels to one or more sensory output devices for presentation to the user;

a sensor data receiver for receiving feedback data comprising electrical activity data representative of brainwave activity of the user;

the brainwave activity of the user being measured using a technique which comprises electroencephalography (EEG) or functional magnetic resonance imaging, an electronic processor configured to normalize the electrical activity data into an index value and to determine in substantially real-time that the index value of the normalized electrical activity data is within a threshold range; and a content selector configured to select content to be outputted by the stimulus output from a plurality of stored content data segments, the content selector configured to select a second type of content based on detecting the index value is within the threshold range, the content selector configured to select the first type of content based on detecting the index value is outside the threshold range;

the threshold range indicates that the user is in a trance state to receive the second type of content, the trance state indicating that the user is in a state of absorbed, focused and attentive neurological state, the first type of content is configured to relax and put the user in an absorbed, focused and attentive neurological state for receiving the second type of content; the second type of content is configured to provide the user with instructional content; and an electronic memory for storing the first and second types of content.

48. A hypnosis device for controlling administration of a hypnosis experience to a user, the hypnosis device comprising:

a stimulus output for outputting a first type of content via one or more media channels to one or more sensory output devices for presentation to the user;

a sensor data receiver for receiving feedback data comprising electrical activity data representative of brainwave activity of the user;

the brainwave activity of the user being measured using a technique which comprises electroencephalography (EEG) or functional magnetic resonance imaging, an electronic processor configured to normalize the electrical activity data into an index value and to determine in substantially real-time that the index value of the normalized electrical activity data is within a threshold range;

a selecting means for selecting content to be outputted by the stimulus output from a plurality of stored content data segments, the selecting means configured to select a second type of content based on detecting the index value is within the threshold range, the content selector configured to select the first type of content based on detecting the index value is outside the threshold range;

the threshold range indicates that the user is in a trance state to receive the second type of content, the trance state indicating that the user is in a state of absorbed, focused and attentive neurological state, the first type of content is configured to relax and put the user in an absorbed, focused and attentive neurological state for receiving the second type of content; the second type of content is configured to provide the user with instructional content;

an electronic memory for storing the first and second types of content;

a learning means arranged to learn using the feedback data which content data segments, after the content data segments have been outputted to the user, are the most effective data segments for encouraging the user to progress through a current stage of a hypnosis session; and a storing means for storing the most effective content data segments in a database record associated with the user.

\* \* \* \* \*